US006191853B1

United States Patent
Yamaguchi et al.

(10) Patent No.: US 6,191,853 B1
(45) Date of Patent: Feb. 20, 2001

(54) APPARATUS FOR MEASURING PARTICLE SIZE DISTRIBUTION AND METHOD FOR ANALYZING PARTICLE SIZE DISTRIBUTION

(75) Inventors: Tetsuji Yamaguchi; Tatsuo Igushi, both of Kyoto (JP)

(73) Assignee: Horiba, Ltd., Kyoto (JP)

(*) Notice: Under 35 U.S.C. 154(b), the term of this patent shall be extended for 0 days.

(21) Appl. No.: 09/406,499

(22) Filed: Sep. 28, 1999

(30) Foreign Application Priority Data

Sep. 29, 1998 (JP) .................................. 10-275438
Oct. 30, 1998 (JP) .................................. 10-309978
Oct. 30, 1998 (JP) .................................. 10-310063

(51) Int. Cl.$^7$ .................................................. G01N 15/02
(52) U.S. Cl. .......................... 356/336; 356/337; 356/338; 250/575
(58) Field of Search ..................... 356/336, 337, 356/338, 335, 339, 340–343; 250/575, 524

(56) References Cited

U.S. PATENT DOCUMENTS

| | | | | |
|---|---|---|---|---|
| 4,158,234 | * | 6/1979 | Grandchamp | 356/336 |
| 4,762,413 | * | 8/1988 | Namba et al. | 356/339 |
| 4,781,460 | * | 11/1988 | Bott | 356/336 |
| 4,828,388 | * | 5/1989 | Namba | 356/366 |
| 5,684,583 | * | 11/1997 | Abe et al. | 356/335 |
| 5,955,139 | * | 9/1999 | Meyer et al. | 356/338 |

* cited by examiner

Primary Examiner—Frank G. Font
Assistant Examiner—Sang H. Nguyen
(74) Attorney, Agent, or Firm—Oppenheimer Wolff & Donnelly LLP

(57) ABSTRACT

An apparatus and method for measuring a particle size distribution comprising a light source directing a laser light to particles which are dispersed into a solvent and which exhibit Brownian motion, a detector converting an interference light caused by Doppler-shifted scattered light by the particles into an electric detection signal, an operation unit obtaining an intermediate function by processing the detection signal, and a processing unit subjecting the intermediate function to an inverse problem and thereby calculating a particle size distribution. The apparatus includes a data selecting unit between the operation unit and the processing unit for selecting data from all data regions in the intermediate function at appropriate intervals and creating a data table used in an inverse problem.

12 Claims, 11 Drawing Sheets

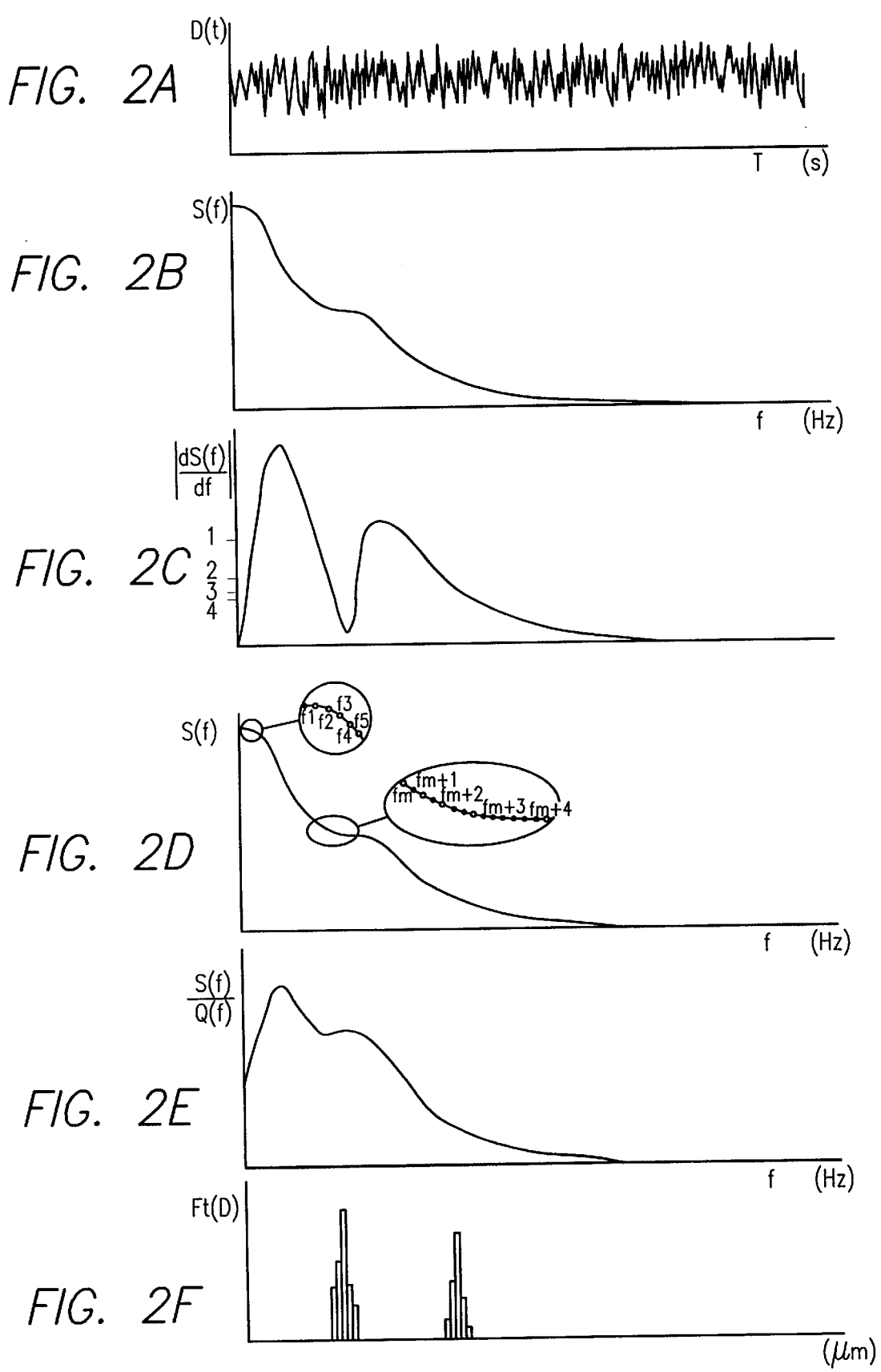

APPARATUS FOR MEASURING PARTICLE SIZE DISTRIBUTION AND METHOD FOR ANALYZING PARTICLE SIZE DISTRIBUTION

BACKGROUND OF THE INVENTION

1. Field of the Invention

The present invention relates to an apparatus for measuring particle size distribution and method to calculate particle size distribution of particles dispersed in a solvent.

2. Description of the Prior Art

Conventionally, there has been conducted a method for directing a laser light to particles dispersed in a solvent, detecting a scattered light from the particles by a detector, counting the detected scattered light to thereby measure the particle size distribution of the particles (which method is normally referred to as photon correlation spectroscopy (PCS)). With PCS, however, it is necessary to set some ranges of sampling time in advance and then measure the limits of the particle size ranges. In addition, to provide a wide measurement range for measuring large particles, it is necessary to make measurements while keeping the particles in a stable state for a long period. Besides, with this method, it is necessary to measure a particle size distribution in a diluted state so that scattered lights do not superpose one another.

To resolve these faults, there has been proposed measuring a particle size distribution by detecting an interference light due to scattered lights caused by the Doppler-shifted laser light directed to particles moving by Brownian motion and Fourier-transforming the detection signal of the interference light to thereby analyze the frequency. In general, in order to compute particle size distribution from power spectrum, an inverse problem for solving Category 1 Fredholm's integral equation which is a relative equation between the power spectrum, the response function, and the particle size distribution is performed.

For example, operation and display divisions by logarithmically dividing a measurement range into m sections are determined in advance. The particle size distribution F(D) (D=1 to m) indicating the number of particles of typical particle sizes in the operation/display section is obtained from light intensity frequency characteristics G. In other words, the relationship between frequency characteristics G(D) (D=1 to m) and the particle size distribution F(D) can be expressed as an equation of $F=P^{-1}G$, where P is a response function. The inverse matrix $P^{-1}$ of the response function is obtained and $F=P^{-1}G$ is operated to thereby acquire the particle size distribution F(D).

In this method, by calculating detection signals by Fourier-transform to get a power spectrum, the particle size distribution can be measured even if the number of particles present in a solvent is large and scattered lights superpose one another. Also, since a wide range measurement can be made for relatively short measurement time, fast and stable measurement is made possible compared to PCS.

It is desirable that the detection signal of an interference light which has been sampled at high speed is used in the power spectrum. Since the resultant data is wide in range, mass storage memory is required. Further, when subjecting the sampled data to deconvolution or inverse problem and the data in a wide range is used as it is, an operation unit requires a mass storage memory and high processing speed.

In consideration of this point, for example, in Japanese Patent Application Laid-open Publication No. 170844/1991 (hereinafter to be referred to as known example), deconvolution of power spectrum was practiced in such procedures that the power spectrum is converted into the form of convolution integration which can be readily inverted by linear transformation by converting the power spectrum into a logarithmic equal distance form, followed by inversion of it. That is to say, the power spectrum is converted by treating the frequency by logarithmic frequency, and the particle size by logarithmic particle size, by which a shift variant response function is made on non-dimensional logarithmic frequency axis, by which there was realized deconvolution integration with which operation can be processed in more simple procedure.

However, in case of converting the power spectrum into a logarithmic equal distance form, it has been unavoidable to thin out the majority part of the sampled data in the stage of converting into logarithmic equal distance.

FIG. 12A–D illustrate general processing methods for performing deconvolution operation or inverse problem from the detection signal of the measured interference light. FIG. 12A shows detection signals of scattered light, FIG. 12B shows a power spectrum (frequency distribution) which is calculated by the detection signals using Fourier transform, FIG. 12C shows a power spectrum calculated by a smoothing calculation from FIG. 12B after the scattered light has been smoothed. The power spectrum gives Lorentzian function indicating the intensity distribution of Brownian motion frequency in accordance with particle sizes. The power spectrum is subjected to deconvolution or inverse problem to thereby calculate a particle size or particle diameter distribution as shown in FIG. 12D.

In the power spectrum shown in FIG. 12B, however, there are influences such as the vibration noise of the solvent, white noise such as noise included in the output of the detector, the amplifier, and the electric circuit, or noise from the power supply line. Normally, the level of vibration noise is almost proportional to the inverse number of the frequency, so that a high level of noise tends to appear in low frequency areas in the power spectrum.

Due to this, if a particle size distribution is to be obtained from the power spectrum including the noise as shown in FIG. 12B, a particle size distribution Fs having different particle sizes and shifted from a true particle size distribution Ft indicated by a virtual line in FIG. 12D may be outputted or an immaterial particle size distribution Fg which does not originally exist may be outputted.

Considering this drawback, there is proposed removing the influence of noise as much as possible by, for example, integrating the power spectrum obtained as shown in FIG. 12C and the particle (diameter) size distribution and by performing smoothing. To remove noise with smoothing, however, it is necessary to carry out processing in a smoothing routine, which processing takes a lot of time. As a result, it has been difficult to make a real-time measurement with this method. Besides, with such smoothing performed, it is difficult to sufficiently remove the influence of noise in, particularly, a low frequency range and measurement accuracy has its limit.

In addition, if sampled data is selected at equal logarithmic intervals and the number of data points to be dealt with is reduced in order to increase processing speed, it is feared that errors may occur in the selection step as shown in FIG. 12C. That is, the power spectrum, shown by ● marked points in FIG. 12C, has values of discontinuous intervals in accordance with sampling speed. Thus, while passing through true values indicated by a solid line, the ● marked points do not often superpose on the O marked logarithmic selection points. For that reason, it is necessary to obtain the data of selection points which do not superpose on the ● marked points by performing interpolation processing as indicated by a virtual line. The values obtained by this operation may be, however, shifted from actual values.

To avoid this drawback, the original data, which is converted into a power spectrum, may be sampled at a higher frequency. If the sampling frequency is high, it is required to employ components with higher-speed performance and the cost of the components increases accordingly. Thus, this method turns out to be impractical.

Moreover, as shown in an enlarged view B of FIG. 12C, where intervals of logarithmic selection points (O marked points) are wide, there often exist important portions for creating a power spectrum curve in the non-selected areas. Due to this, a polygonal line connecting selection points, as indicated by a two-dot chain line, may greatly differ from actual values. This has caused errors at the time of subjecting the particle size distribution to a deconvolution or an inverse problem.

Additionally, in the conventional deconvolution or inverse problem method using matrix calculation, vibration and divergence normally tend to occur when obtaining solutions of a particle size distribution matrix F. If vibration and divergence occur in a vector operation, immaterial peaks may be generated in the particle size distribution F. To prevent this, there is proposed adding a matrix to determine converging conditions for the distribution configuration and curve of the particle size distribution F. The matrix to determine converging conditions is difficult to acquire, resulting in complicated operation processing.

Further, the response function P varies according to measurement conditions such as the viscosity, refraction index and temperature of the solvent at the time of obtaining the particle size distribution F. As stated above, due to the need to perform complicated operation processing, there is no avoiding fixing the response function obtained as theoretical values and disadvantageously lowering the analysis accuracy of the method accordingly.

Moreover, in the above-stated inverse problem method, m operation and display sections obtained by logarithmically dividing a measurement range are set in advance and they are determined in accordance with the number of divided sections made by a detector and calculation conditions of the apparatus mentioned above. Since the number of divided sections made by a detector and the calculation conditions of the apparatus mentioned above are fixed, users cannot freely change operation and display sections. In other words, the users cannot widen an operation and display width in the particle size distribution, even if they consider it necessary, to obtain a particle size distribution with required accuracy, or cannot widen a division width used for the operation to increase operation speed.

In addition, there is no definite criteria for determining such operation and display sections and, in many cases, the width and number of operation display sections vary depending on the apparatus. Thus, unified criteria cannot be expected. Besides, the display formats for displaying operation results differ among equipment, that is, the formats for displaying the horizontal scales not only linearly but also logarithmically differ among equipment, and users cannot freely select a display format. In other words, the users cannot compare the display of a particle size distribution outputted by one equipment with that by another at all.

SUMMARY OF THE INVENTION

The present invention has been made in consideration of the above circumstances. It is, therefore, an object of the present invention to provide a particle size distribution measurement apparatus and a particle size distribution analysis method capable of obtaining a highly accurate particle size distribution in view of conditions at the time of measurement including information obtained depending on measurement conditions and particle sizes, capable of enhancing the accuracy of calculating the particle size distribution and improving reproducibility without performing complicated operation processing and allowing a user to freely change the number of divisions and display widths for operation and display sections within a display range.

To attain the above objective, an apparatus for measuring a particle size distribution according to a first embodiment comprises a light source directing a laser light to particles which are dispersed into a solvent and which exhibit Brownian motion; a detector converting an interference light caused by Doppler-shifted scattered light by the particles into an electric detection signal; an operation unit obtaining an intermediate function by processing the detection signal; and a processing unit subjecting the intermediate function to an inverse problem and thereby calculating a particle size distribution. A data selecting unit is provided between the operation unit and the processing unit for selecting data from all data regions in the intermediate function at appropriate intervals and creating a data table used in the inverse problem.

Thus, the data selected to create a data table used for operation is selected from all data regions at appropriate intervals. Due to this, there is no need to perform an interpolation operation for points which lack data, and the inverse problem is performed without using data shifted from true values. The term "inverse problem" herein refers to the act of obtaining a particle size distribution from Category 1 Fredholm's integral equation, and it is different from the inverse problem for obtaining the particle size distribution from the convolution integration.

In addition, the data selection unit may include a differential step for operating absolute values obtained by first-differentiating the intermediate function and a selection part for selecting data from all data regions at intervals, the intervals becoming shorter as an operation result of the differential step shows that the absolute value is higher and the intervals becoming longer as the operation result shows the absolute value is lower. Alternatively, the data selection unit may include a differential step for operating an absolute value obtained by second-differentiating the intermediate function, and a selection step for selecting data from all data regions at intervals, the intervals becoming shorter as an operation result of the differential step shows that the absolute value is higher and the intervals becoming longer as the operation result shows that the absolute value is lower.

In either case, it is possible to thin out data having good reproducibility by selecting a small quantity of data. Thus, even with a small quantity of data, it is possible to measure a particle size distribution with high accuracy. That is, it is possible to enhance the measurement accuracy of particle size distribution and to increase operation speed as much as possible. Furthermore, even if the data sampling frequency used for operating the particle size distribution is controlled compared with the conventional apparatus, it is possible to measure the particle size distribution with sufficient accuracy.

A method for measuring a particle size distribution according to a second embodiment comprises the steps of directing a laser light to particles which are dispersed into a solvent and which exhibit Brownian motion; converting an interference light caused by Doppler-shifted scattered light by the particles into an electric detection signal; processing the detection signal to obtain an interim function, followed by inverse problebming this interim function to calculate the particle size distribution. The second embodiment further comprises the steps of selecting data from all data regions in the intermediate function at appropriate intervals; creating a data table used in an inverse problem; and obtaining the particle size distribution from the table.

In addition, the method may include steps of operating an absolute value obtained by first-differentiating the intermediate function; creating a data table and selecting data from all data regions at intervals, the intervals becoming shorter as an operation result of the differential step shows that the absolute value is higher and the intervals becoming longer as the operation result shows the absolute value is lower. Alternatively, the method may include the steps of operating an absolute value obtained by second-differentiating the intermediate function; creating a data table and selecting data from all data regions at intervals, the intervals becoming shorter as an operation result of the differential step shows that the absolute value is higher and the intervals becoming longer as the operation result shows that the absolute value is lower.

A method for analyzing a particle size distribution according to a third embodiment comprises the steps of directing a laser light to particles which are dispersed into a solvent and which exhibit Brownian motion; converting an interference light caused by Doppler-shifted scattered light by the particles into an electric detection signal; subjecting the intermediate function to an inverse problem and thereby calculating a particle size distribution. The third embodiment further comprises the steps of, while presetting an assumed particle size distribution, calculating frequency characteristics of the detection signal and setting the frequency characteristics as measured frequency characteristics; calculating frequency characteristics of Lorenzian function having a half band width obtained by a Stokes-Einstein expression from measurement conditions in accordance with particle sizes and setting the frequency characteristics of Lorenzian function as operation frequency characteristics; calculating a response function indicating a light intensity with respect to a particle size based on the operation frequency characteristics for every frequency; calculating the frequency characteristics based on assumed values in the assumed particle size distribution for every frequency using the response function as a weight; correcting the assumed particle size distribution in accordance with a rate of a difference between the frequency characteristics based on the assumed values and the measured frequency characteristics; repeating the processing steps using the corrected assumed particle size distribution; and determining, as a true particle size distribution, the assumed particle size distribution when the rate of the difference between the frequency characteristics based on the assumed values and the measured frequency characteristics falls within a predetermined range.

Thus, the response function is calculated by the Stokes-Einstein expression in accordance with measurement conditions. Due to this, the fine adjustment of the response function can be made in accordance with the index of refraction, viscosity and temperature of a solvent as well as the wavelength of the laser light directed to the particles and the angle of a detected spattered light, thereby making it possible to operate the distribution with high accuracy. Moreover, the computer can satisfactorily compare the frequency distribution based on the assumed particle size distribution with the measured frequency distribution and repeat the comparison while correcting the assumed particle size distribution. Owing to this, unlike the conventional method, vibration and divergence do not occur, thereby making it possible to attain a true particle size distribution.

A method for analyzing a particle size distribution according to a fourth embodiment comprises the steps of directing a laser light to particles which are dispersed into a solvent and which exhibit Brownian motion; converting an interference light caused by Doppler-shifted scattered light by the particles into an electric detection signal; and subjecting the intermediate function to an inverse problem and thereby calculating a particle size distribution. The fourth embodiment further comprises the steps of, while presetting an assumed particle size distribution, calculating an autocorrelation function of the detection signal and setting the autocorrelation function as a measured autocorrelation function; calculating an autocorrelation function of an exponential function having a time constant obtained by a Stokes-Einstein expression from measurement conditions in accordance with a particle size and setting the autocorrelation function as an operation autocorrelation function; calculating a response function indicating a light intensity with respect to a particle size based on the operation autocorrelation function for every delay time; calculating the autocorrelation function based on assumed values in the assumed particle size distribution for every delay time using the response function as a weight; correcting the assumed particle size distribution in accordance with a rate of a difference between the autocorrelation function based on the assumed values and the measured autocorrelation function; repeating the processing steps using the corrected assumed particle size distribution; and determining, as a true particle size distribution, the assumed particle size distribution when the rate of the difference between the autocorrelation function based on the assumed values and the measured autocorrelation function falls within a predetermined range.

Thus, the response function is calculated in accordance with measurement conditions. Owing to this, it is possible to operate the particle size distribution with high accuracy and to obtain a true particle size distribution without causing vibration and divergent as in the conventional apparatus. Besides, by converting the measured light intensity into an autocorrelation function, it is possible to effectively remove noise components included in the detection signal and to thereby further enhance measurement accuracy.

If an operation and display range of the particle size distribution are divided into sections, each having an appropriate division width selected by a user and typical particle sizes for the respective sections are determined; and if the number of particles of respective typical particle sizes on a true particle size distribution obtained while using the number of particles of the respective typical particle sizes as an assumed particle size distribution in the above-stated particle size distribution analysis method is displayed, then the user can appropriately select a division width, divide the operation and display region and use the divided sections in the operation. For instance, if high resolution is required, it is possible to increase the number of divisions. If high resolution is not required, it is possible to decrease the number of divisions and thereby increase speed for completing the operation. Besides, it is possible to easily compare the obtained measurement result with that measured in another apparatus.

In the case of converting the detection signal into an autocorrelation function, in particular, it is possible to easily remove noise components included in the detection signal and to enhance the analysis accuracy of the particle size distribution.

If the division widths, division numbers and display widths for the respective sections in a table are stored; if the response function is operated and if the assumed particle size distribution in accordance with a division number and a division width selected from the table are corrected; and if the number of particles of the respective typical particle sizes in accordance with the selected display width are displayed, then the division widths, division numbers and display widths can be easily selected to thereby enhance operability.

In other words, according to the present invention, in any of these cases, by employing the optimum operation method, complicated operation can be evaded and operation speed can be increased. Also, it is made possible to practice an inverse problem from Category 1 Fredholm's integral equation of a non-linear subject which has so far been considered impossible to practice due to complexity, and it is possible to carry out operation to obtain particle size distribution in as high precision as possible.

BRIEF DESCRIPTION OF THE DRAWINGS

FIGS. 2A through 2F are an explanatory view for explaining the processing contents of respective parts of the measuring apparatus shown in FIG. 1; wherein FIG. 2A shows a detection signal; FIG. 2B shows a power spectrum; FIG. 2C shows absolute values obtained by first-differentiating the power spectrum; FIG. 2D determination of an extract point of the data of power spectrum of FIG. 2B according to the size of the differentiation value of FIG. 2C; FIG. 2E shows a quotient of division of the power spectrum of FIG. 2D by the weight function of response function; and FIG. 2F shows a particle size distribution;

FIGS. 8A through 8D are an explanatory view for explaining the processing contents of respective parts of the measurement apparatus shown in FIG. 7, wherein FIG. 8A shows detection signals, FIG. 8B shows a power spectrum; FIG. 8C shows absolute values obtained by first-differentiating the power spectrum; and FIG. 8D shows a particle size distribution;

FIG. 9A shows a power spectrum; FIG. 9B shows absolute values of the first differentiated power spectrum; FIG. 9C shows absolute values obtained by second-differentiating the power spectrum; and FIG. 9D shows a particle size distribution;

FIGS. 10A through 10C are explanatory views for explaining another modified example of the measurement apparatus, wherein FIG. 10A shows an autocorrelation function; FIG. 10B shows absolute values obtained by first-differentiating the autocorrelation function; and FIG. 10C shows a particle size distribution;

FIG. 12 is an explanatory view for explaining the processing contents in a conventional particle size distribution apparatus, wherein

DETAILED DESCRIPTION OF THE PREFERRED EMBODIMENTS

Figure 1:
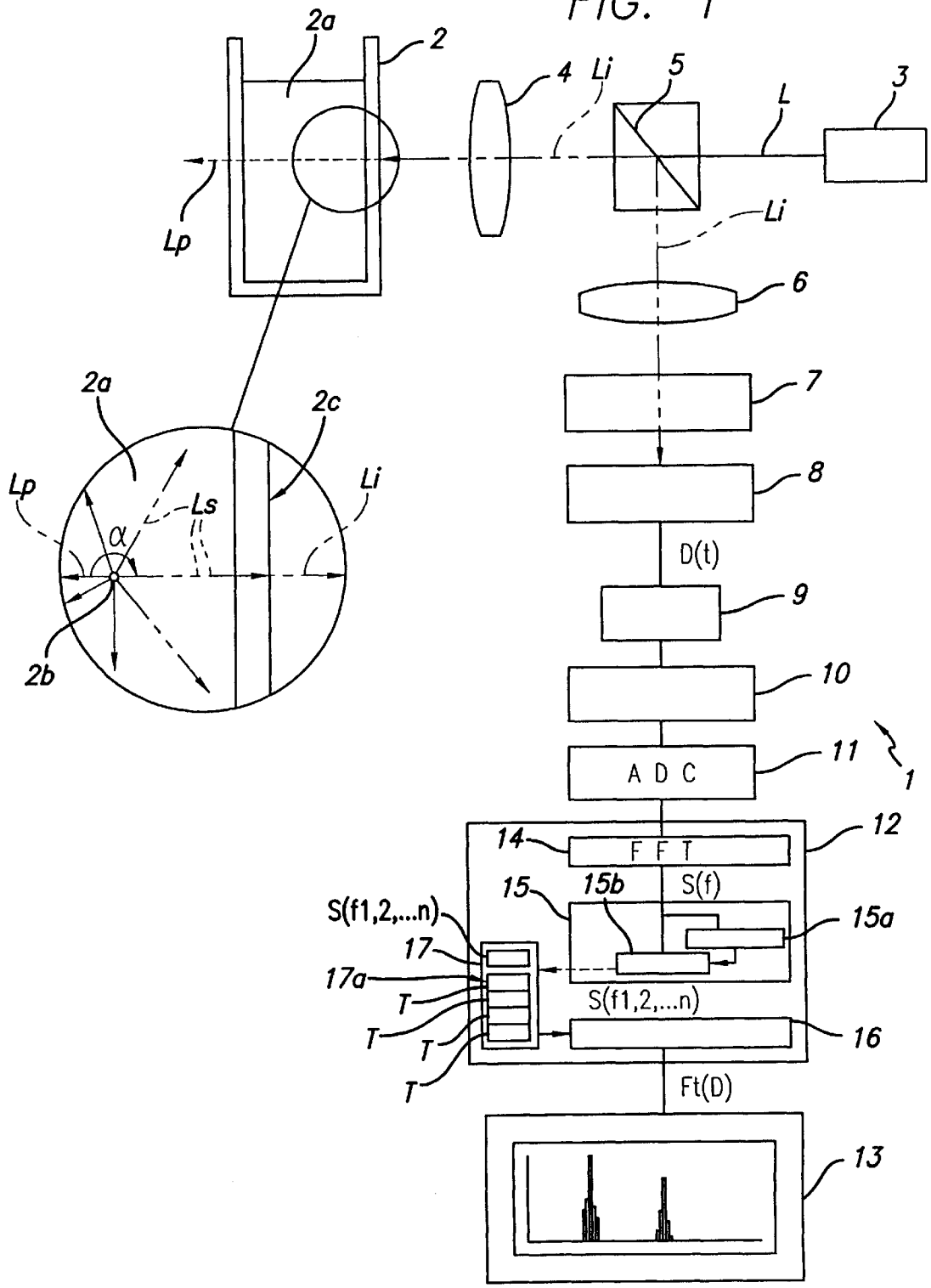
FIG. 1 is a block diagram of a particle size distribution measurement apparatus in accordance with a preferred embodiment of the present invention.

FIG. 1 is a block diagram of a particle size measurement apparatus in accordance with a first embodiment of the present invention. In FIG. 1, reference numeral 2 denotes a cell containing a solvent 2a and measurement target particles 2b, reference numeral 3 denotes a light source for directing a laser light L to the particles 2b, reference numeral 4 denotes a lens converging the laser light L into the cell 2, reference numeral 5 denotes a beam splitter for reflecting an interference light Li caused by the Doppler shifted scattered lights by the particles 2b, reference numeral 6 denotes a lens converging the interference light Li and reference numeral 7 denotes a polarizing plate. The reference numeral 5 should not be limited to a beam splitter. It may be a reflecting mirror with a hole.

Reference numeral 8 denotes a detector for converting the interference light Li into a electric detection signal, reference numeral 9 denotes an amplifier amplifying the detection signal, reference numeral 10 denotes a filter, reference numeral 11 denotes an A/D converter converting a detection signal D(t) into a digital signal, reference numeral 12 denotes a data processing unit for subjecting the detection signal D(t) to data processing to obtain a particle size distribution Ft(D) and reference numeral 13 denotes a display unit displaying the particle size distribution Ft(D) obtained by the display unit 13.

The data processing unit 12 consists of an operation sub-unit (to be referred to as 'FFT' hereinafter) 14 for obtaining a power spectrum S(f) by Fourier-transforming signal D(t) of an interference light, a data selecting subunit 15 for selecting data at appropriate intervals from all of the data on the obtained power spectrum S(f) and creating a data table $S(f_{1, 2, 3 \ldots n})$, a processing sub-unit 16 for obtaining the particle size distribution of the particles from the data table $S(f_{1, 2, 3 \ldots n})$, and an apparatus operating sub-unit 17 for operating the processing sub-unit 16. The data selecting part 15 consists of a differential sub-unit 15a for differentiating the power spectrum S(f) and operating the absolute value thereof and a selecting sub-unit 15b for selecting data $S(f_1), S(f_2), \ldots, S(f_n)$ necessary for the creation of the data table $S(f_{1, 2, 3 \ldots n})$ from all of the data on the power spectrum S(f) in accordance with the gradient of the power spectrum S(f) using the operation result.

With this structure, the laser light L emitted from the laser light source 3 passes through the beam splitter 5 and the lens 4 and is condensed into the cell 2. At this moment, as shown in an enlarged view of FIG. 1, part of the laser light L (non-scattered light) is reflected and scattered on a wall surface 2c of the cell 2. The laser light Lp passes through the wall surface 2c and strikes against the particles 2b moving by Brownian motion and dispersed in the solvent 2a, and a laser light Ls (scattered light) Doppler-shifted by the Brownian motion is scattered. The scattered light Ls interfere with each other and turn into an interference light Li, which is condensed onto the detector 8 after passing through the lens 3, beam splitter 5, lens 6 and the polarizing plate 7.

The interference light Li should not be limited to an interference light Li resulting from scattered lights Ls interfering with each other. It may be an interference light Li obtained when the reflection light on the wall surface 2c and the above-stated scattered light Ls interfere with each other.

That is, the angle α of the interference light Li with respect to the incident laser light L is 180°. The polarizing plate 7 cuts lights other than those reflected by the beam splitter 5 using directional polarization. The interference light Li is condensed into an electric detection signal D(t) by the detector 8, amplified by the amplifier 9, filtered by the filter 10 and then converted into a digital value by the A/D converter 11. The laser light L reflected and scattered on the wall surface 2c and the scattered laser light Ls are also condensed onto the detector 8. Since they are high-frequency lights, DC components in the lights are cut by the filter 10.

FIGS. 2A through 2F show an explanatory view at the respective sections in a case where the particles 2b have two diameters. FIG. 2A shows detection signals D(t). FIG. 2B shows the power spectrum (that is, measured frequency characteristics) S(f) which has been transformed by the FFT calculation 14. FIG. 2C shows a first-differential spectrum of the power spectrum shown in FIG. 2B. The values of vertical axis of FIG. 2C show intervals between selecting data points, for example, every point are selected when the value is 1, one point is selected in 4 data when the vale is 4.

FIG. 2D is a spectrum selected data to calculate a particle size distribution from the power spectrum S(f) of FIG. 2B. The selecting points are decided by the absolute value of the first-differentiating spectrum (FIG. 2C). FIG. 2E shows a spectrum in which the power spectrum of FIG. 2B is divided by a weight function Q(f) of a response function. Q(f) is the maximum height's function of each P(f,D), and Q(f) equals the weight function. A particle size distribution is calculated by the spectrum of FIG. 2E.

The differential power spectrum is created to determine f for selecting data from the power spectrum of FIG. 2B and is not used for deconvolution calculating a particle size distribution. The selecting sub-unit 15b selects data from S(f) accordance with the magnitude of the power spectrum S(f) of FIG. 2C.

With the selected data $S(f_{1, 2, 3 \ldots n})$, a data table S(f1, 2, 3. n) including n data is created as shown in table 1 below. In regards to the table and the enlarged view of FIG. 2D, O mark indicates selected data, and ● mark indicates data not selected. The interval between $f_m$ and $f_{m+1}$ and that between $f_{m+1}$ and $f_{m+2}$ are 2, the interval between $f_{m+2}$ and $f_{m+3}$ is 3 and the interval between $f_{m+3}$ and $f_{m+4}$ is 7.

TABLE 1

Data table

| f | S(f) |
|---|---|
| $f_1$ | $S(f_1)$ |
| $f_2$ | $S(f_2)$ |
| ... | ... |
| $f_n$ | $S(f_n)$ |

The selection interval is based on the corresponding FIG. 2C, i.e., if the power spectrum S(f) of FIG. 2B has a steep gradient, the intervals are short and if it has a slight gradient, the intervals are long. The vertical axis of FIG. 2C shows an example of selection intervals corresponding to the gradient of the power spectrum S(f) of FIG. 2B.

Thus, all of the selection points $f_1$ through $f_n$ are true values measured and there is no need to interpolate data as done in the conventional apparatus.

Namely, it is possible to prevent the points from being shifted from true values due to interpolation processing. Furthermore, data selection intervals are narrowed in accordance with the intensity of the gradient of the power spectrum S(f). Due to this, at portions where the gradient of the power spectrum S(f) varies so much that the intervals are narrowed to thereby improve data reproducibility. At portions where the gradient varies slightly, data is roughly selected to thereby allow making the speed of later operation processing faster.

FIG. 2F shows a particle size distribution Ft(D) obtained by performing an inverse problem (to solve inversely the relation of Category 1 Fredholm's integral equation to calculate the particle size distribution from the power spectrum) based on the data in the data table $S(f_{1, 2, 3 \ldots n})$ thus selected. A power spectrum is convolution's relationship between a particle size distribution and a response function. If we measure a power spectrum for some particle, the particle size distribution will be calculated by the power spectrum in this relationship. The particle size distribution Ft(D) can be calculated at intervals selected by a user and obtained as a linearly divided particle size distribution Ft(D).

As stated above, according to the particle size distribution measurement apparatus 1 of the present invention, there is no need to operate the enormous quantity of data as in the case of subjecting all the data of the power spectrum S(f) to an inverse problem. Thus, a computer, which is not shown, does not require a mass storage memory for operation processing and high-speed inverse problem is made possible.

In addition, data is not selected logarithmically but in accordance with the gradient of the power spectrum S(f). That is, data is selected minutely at portions where variation is sharp, whereas data is selected roughly at portions where variation is slow. In other words, an inverse problem is conducted using the data in the data table $S(f_{1, 2, 3 \ldots n})$ at optimum intervals, so that a highly accurate particle size distribution can be calculated even if the number of data is reduced, and it is possible to prevent the deterioration of reproducibility resulting from the decreased number of data as much as possible.

In addition, selected data table $S(f_{1, 2, 3 \ldots n})$ is always a true value measured, thereby enhancing measurement accuracy compared with the conventional apparatus. Besides, since it is not necessary to operate interpolated data, there is no need to use a very high-speed A/D converter 11 for converting a detection signal D(t) into a digital signal for the purpose of enhancing the accuracy of interpolation. It is possible to reduce the production cost for the particle size distribution measurement apparatus 1 accordingly. In short, operation with good reproducibility is carried out using a minimum apparatus and measurement values, so that the capacity of the memory necessary for operation can be reduced, high-speed operation can be realized and measurement accuracy can be improved.

In each of the above-stated embodiments, an example of measuring particles of two sizes is given for the convenience of description. Needless to say, the present invention should not be limited to the example described. For instance, it is possible to measure a particle size distribution at high accuracy and high speed even if monodisperse particles or polydisperse particles of three sizes of more are measured.

In either case, according to the present invention, intervals of data selection points are determined based on the gradient or change of gradient of the power spectrum S(f). Thus, it is possible to optimize selection point intervals and to provide a highly accurate particle size distribution.

FIG. 3 shows examples of the true particle size distribution Ft(D) displayed on a display unit 13. Specifically, FIG. 3A shows that the division width d is set at an equal width $d_1$ to provide high resolution, the number of division $m_1$ increases and the display width (horizontal axis) is set linearly. As in this case, it is possible to analyze a particle size distribution more minutely and to thereby increase resolution by narrowing the division width $d_1$.

Figure 3A:
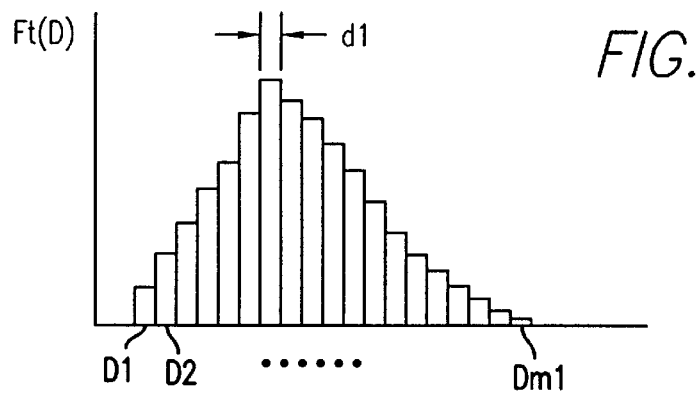
FIG. 3 is a view showing an example of output of the particle size distribution according to the above method for analyzing the particle size distribution.
Figure 3B:
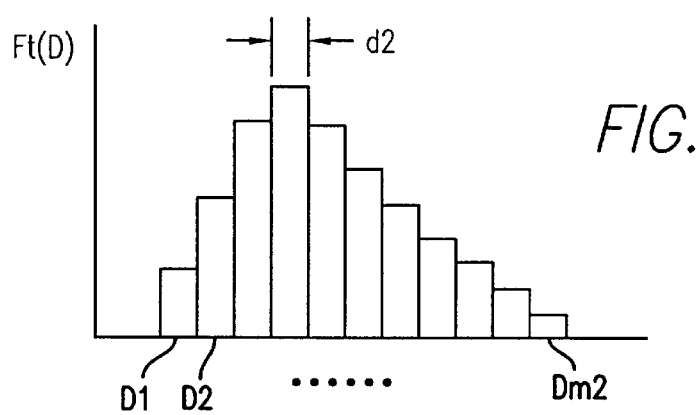

In case of FIG. 3B, the division width d may be large with an equal width $d_2$, the number of divisions $m_2$ may decrease and the display width may be set linearly. In this case, it is possible to shorten the time required for analyzing the particle size distribution as stated above since the division number is low. This is particularly useful if high resolution is not required.

Figure 3C:
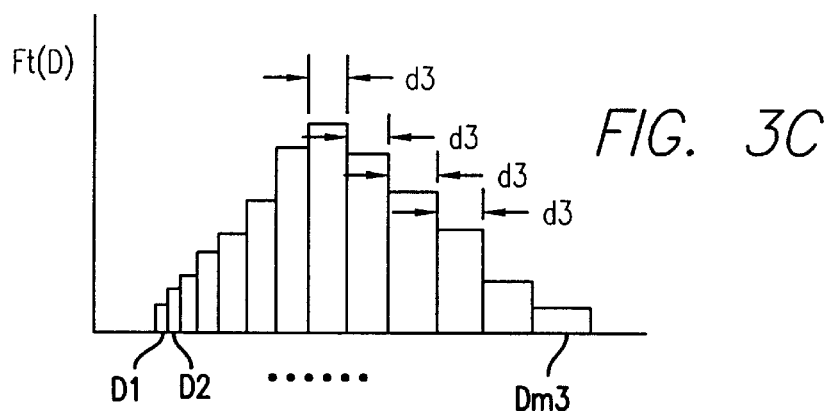
Figure 3D:
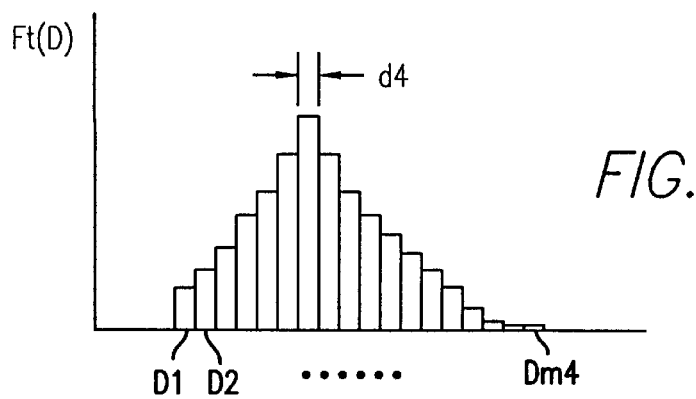

FIG. 3C is a display example of the particle size distribution Ft(D) in a case where a division width $d_3$ is logarithmically changed and the display width (horizontal axis) is set equally (or linearly). FIG. 3D is a display example of the particle size distribution Ft(D) in a case where both the division width d4 and the display width (horizontal axis) are set to have an interval logarithmically changed. As in this case, calculation time required for particle size distribution analysis can be shortened and necessary resolution can be outputted by changing the division width d logarithmically. Thus, this case is useful for particle size distribution analysis.

In this embodiment, the settings of the division width d, division number and display width (horizontal axis display method) in the operation and display region for particle size distribution analysis as stated above are made in the unit operation sub-unit 17 as the data table T (in this table there are recorded the respective representative particle sizes $D_1$–$D_m$ which are divided into the divisions having optional division widths selected by the user). Therefore, only by selecting a setting option, having necessary resolution and allowing the user to see the display clearly, from the settings prepared as the data table D, the user does not need to set the division width d, division number and display width individually, thereby making setting simple.

Although FIGS. 3A through 3D depict typical settings for division width d, division number and display width, the present invention does not limit the number of data table D settings. It is also possible to store a lot of data tables D to set them according to different types of resolutions, set them so as to allow the particle size distribution to be analyzed more minutely and the like.

In the particle size distribution analysis method according to the present invention, in particular, operation is performed to obtain the response function P(f,D) used for analyzing the particle size distribution in accordance with the division width d, division number and display width freely (i.e., the respective representative particle size $D_1$–$D_m$ which are recorded in Table T) set by the user.

Figure 4:
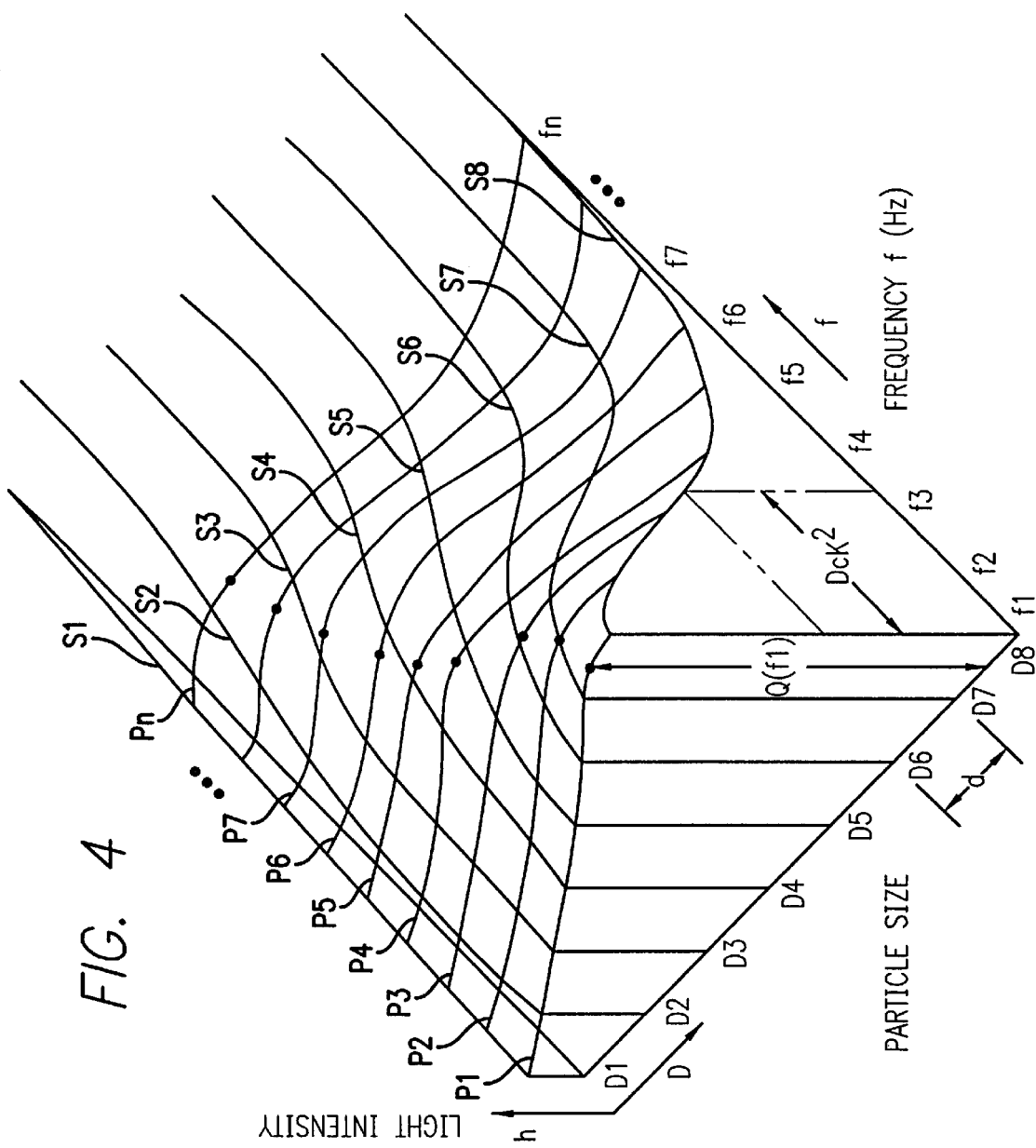
FIG. 4 is a perspective view showing a stereographic graph to illustrate the process for preparing the response function of the present invention.

FIG. 4 is a perspective view representing a method for creating a response function P(f,D) as a three-dimensional graph. In FIG. 4, a h direction indicates light intensity, a f direction indicates frequencies of a detection signal and a D direction indicates particle size.

In this embodiment, particle sizes are classified into typical particle sizes $D_1$ to $D_8$. That is, $S_1$ to $S_8$ indicate operation power spectrums (operated frequency characteristics) for the typical particle sizes $D_1$ to $D_8$, respectively. For helping better understand the gist of this embodiment, only eight types of operation power spectrum S(f)s for the typical particle sizes $D_1$ to $D_8$ are indicated. In actual calculation, however, more operation power spectrums S(f) are calculated so as to enhance measurement accuracy. Needless to say, the present invention does not limit the number of typical particle sizes. Also, the intervals d of the typical particle sizes $D_{1, 2 \ldots 8}$ correspond to the display formats and display intervals set by the user, the data table T as described with reference to FIG. 3.

The operation power spectrums S(f) $S_1$ to $S_8$ of particles for the typical particle sizes $D_1$ to $D_8$ can be obtained in compliance with measurement conditions. That is to say, the operation power spectrums S(f) $S_1$ to $S_8$ are obtained based on a diffusion coefficient $D_c$ which is calculated by using the Stokes-Einstein expression (1) shown below and on a coefficient K which is calculated by using a relational expression (2) also shown below. The operation power spectrums S(f) $S_1$ to $S_8$ are Lorenz functions having a half-width, $2D_cK^2$.

$$D_c = \frac{kTC}{3\pi\mu d} \qquad \text{Expression (1)}$$

$$K = \frac{4\pi}{\lambda} n \sin\frac{\alpha}{2} \qquad \text{Expression (2)}$$

Where k is a Boltzmann constant, T is an absolute temperature, C is a Cunningham's slide correction term, $\mu$ is a viscosity coefficient of the solvent, d is a particle size, $\lambda$ is a wavelength of the laser light L and n is an index of refraction of the solvent. In the example shown in FIG. 1, the angle $\alpha$ is 180° and the above formula (2) is K=$4_\pi$n/$\lambda$.

As stated above, the operation power spectrums $S_1$ to $S_8$ of the typical diameters $D_1$ to $D_8$ are operated and are represented on the h-f plane, respectively. According to the present invention, the operation power spectrums $S_1$ to $S_8$ are calculated in compliance with measurement conditions, operation accuracy can be, therefore, kept high.

Next, referring to the h-D plane of the characteristics, particle size light intensity characteristic curves $P_1$ to $P_n$ represent light intensities with respect to particle sizes. Each of the particle size—light intensity characteristic curves $P_1$ to $P_8$ peaks at a point of a large particle size when a frequency is small and peaks at a point of a small particle size when a frequency is high. Also, the particle size—light intensity characteristic curves $P_1$–$P_n$ need not be the same in configuration and size, respectively. Now, based on particle size—light intensity characteristic curves $P_1$ to $P_n$, response functions indicating relative intensities of light intensities with respect to particle sizes for frequencies $f_1$ to $f_n$ are calculated, respectively. In this embodiment, for the convenience of description, intervals of the frequencies $f_1$ to $f_n$ for calculating the particle size—light intensity characteristic curves $P_1$ to $P_n$ are taken long. Actually, however, operation is performed at minute intervals. It goes without saying that if the intervals are shorter, the measurement accuracy can be further enhanced. The intervals of the frequency f correspond to extraction points in the table shown in Table 1.

Figure 5:
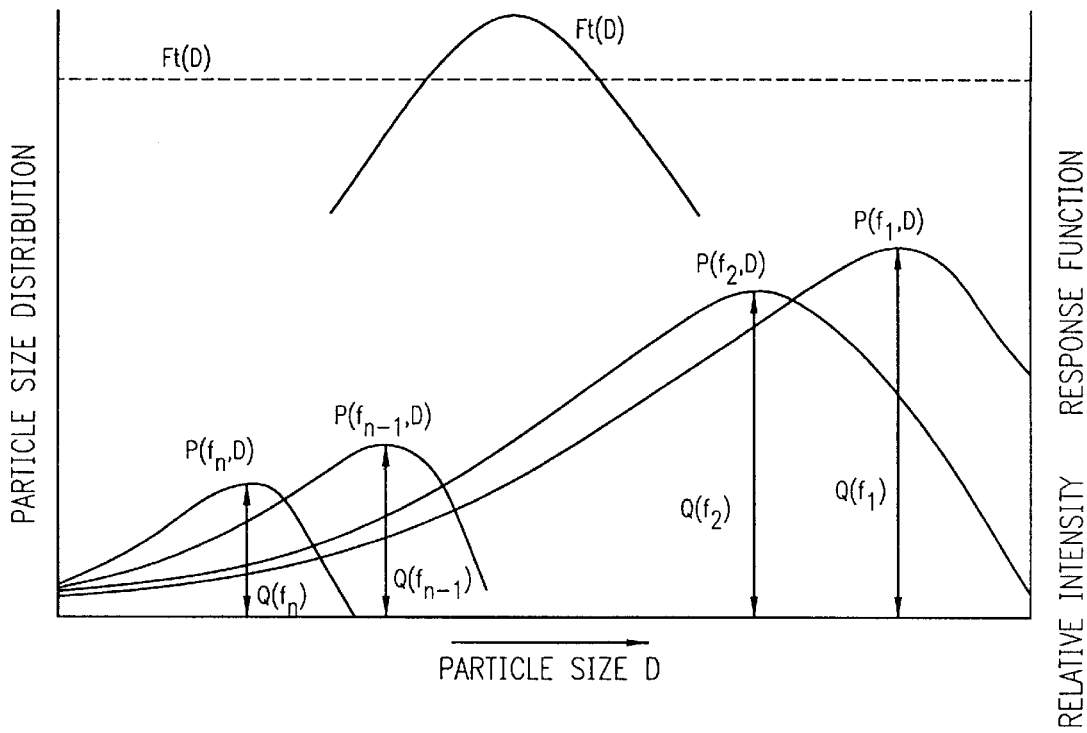
FIG. 5 shows the relationship among an assumed particle size distribution, an actual particle size distribution and a response function in the particle size distribution analysis method.

FIG. 5 shows response functions P(f,D) obtained as stated above. In FIG. 5, F(f,D) indicates an assumed particle size distribution and Ft(D) indicates a true particle size distribution. In this embodiment, the assumed particle size distribution F(D) is initially set, as shown in a virtual line in FIG. 5, for instance, such that the relative intensity is a constant value throughout the range of the particle size distribution.

Q(f) is the maximum height function of each P(f,D), and Q(f) equals the weight function. Every P(f,D) is divided by Q(f), so that the every height of P(f,D) is the same. A measured power spectrum S(f) is divided by Q(f), so that the spectrum is S(f)/Q(f) as shown in FIG. 2E. The P(f,D) and S(f)/Q(f) are used to calculate the particle size distribution.

Figure 6:
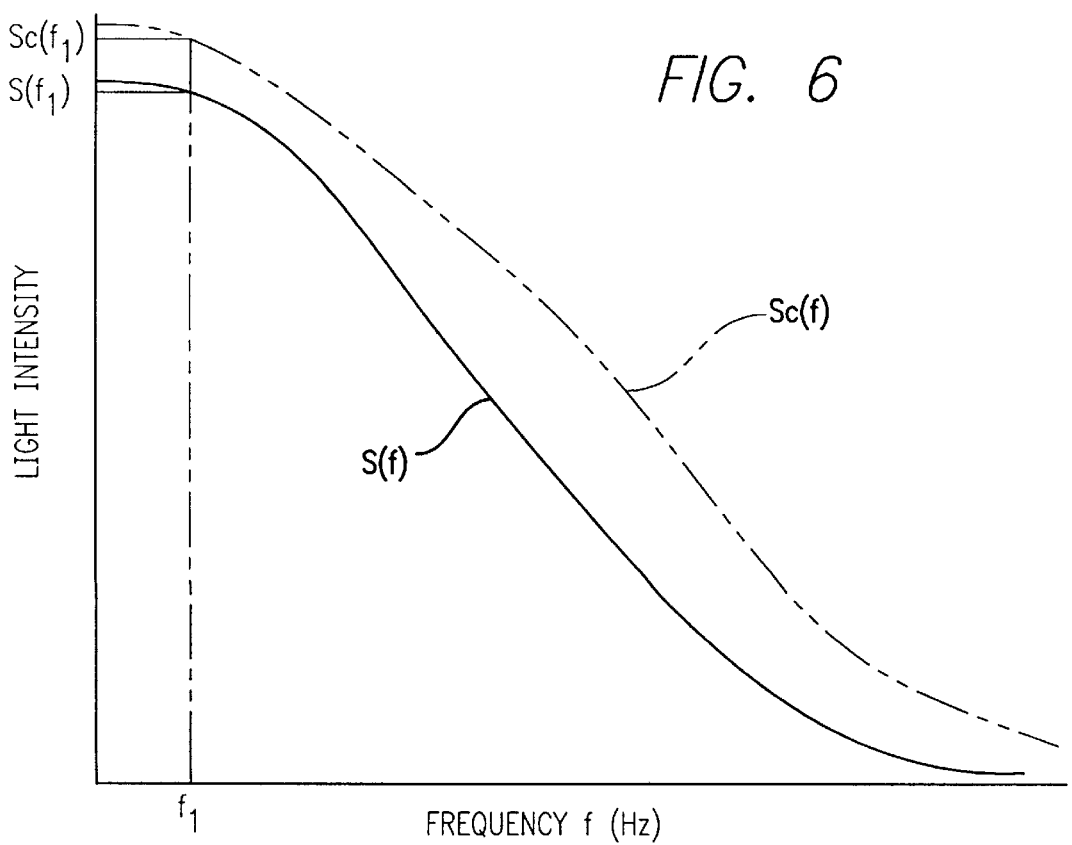
FIG. 6 shows the relationship between assumed value basis frequency characteristics and measured frequency characteristics.

Next, the calculation of a particle size distribution will be described with FIG. 6. The power spectrum Sc(f) based on assumed values is obtained using the above-stated assumed particle size distribution F(D) by operating the following expression (3). When the power spectrum Sc(f) of light intensity based on the assumed value is operated for every frequency f, an operation value $Sc(f_1)$ at a frequency of $f_1$ is calculated by multiplying the assumed particle size distribution F(D) by the response function $P(f_1,D)$ as a weight and then integrated them.

$$Sc(f_1) = \int P(f_1, D) \times F(D)dD \quad \text{Expression (3)}$$

Then, the operation value $Sc(f_1)$ based on the assumed particle size distribution F(D) calculated above is compared with the measured value $S(f_1)$ stored in the data table T of the measured power spectrum S(f). Based on the comparison $r_0 = S(f_1)/Sc(f_1)$, a corrected assumed particle size distribution F'(D) is calculated using the following expression (4) and the assumed particle size distribution F(D) is corrected to F'(D).

$$F'(D) = \{1 + (r_0-1)P(f_1,D)\}F(D) \quad \text{Expression (4)}$$

The above-stated operation processing is repeatedly carried out by changing $P(f_1, D)$ to response functions $P(f_2, D)$ to $P(f_n, D)$ corresponding to the respective frequencies $f_1$, $f_2 \ldots f_n$ and the values of the assumed particle size distribution F(D) are sequentially corrected. If the calculation of the last response function $P(f_n, D)$ is over, the above operation is repeated again, returning to the initial response function $P(f_1 D)$.

If the ratio $r_0$ of the operation value $Sc(f_1)$ of the power spectrum Sc(f) based on the assumed particle size distribution F(D) to the measurement value $S(f_1)$ of the measured power spectrum S(f) is almost 1 with respect to the response functions P(f,D) (where f=1 to n) corresponding to all of the frequencies $f_1, f_2 \ldots f_n$, then the assumed particle size distribution F(D) is displayed on the display unit 13 as a true particle size distribution Ft(D). In this example, when the iteration function in the above operation has reached a certain predetermined number of repetitions, the assumed particle size distribution F(D) is set to be the true particle size distribution Ft(D).

As stated above, according to the present invention, the assumed particle size distribution F(D) is weighed by the response function P(f,D), thereby obtaining the power spectrum Sc(f ) based on assumed values, comparing the power spectrum S(f) with the measured the power spectrum S(f), sequentially repeating correction operations. Thus, it is possible to ensure that the assumed particle size distribution F(D) approaches the true particle size distribution Ft(D). Since neither vibration nor divergence occur during operation processing as shown in the conventional apparatus and method, simple operation is repeatedly carried out by the computer which is well suited for such operation and a particle size distribution F(D) can be calculated with high accuracy without the need to suppress the vibration and divergence by performing complicated operation processing.

In addition, since the response function P(f,D) which plays a vital role in the operation of the particle size distribution is obtained in accordance with varied measurement conditions, it is possible to measure the distribution with high accuracy in accordance with a measurement state.

By allowing the division width d, division number and display width in the operation and display range to be freely set by a user, the measurement value can be compared with that in a different type of equipment having a different resolution, which comparison has been impossible by the conventional method. Thus, it is useful for a case where it is necessary to compare measurement data with the previous one. It is noted that the division width d, division number and display width in the operation and display range are contained in a table to thereby make settings simpler in this embodiment. It is also possible to make division width d, division number and display width variable among typical particle sizes independently of one another.

Figure 7:
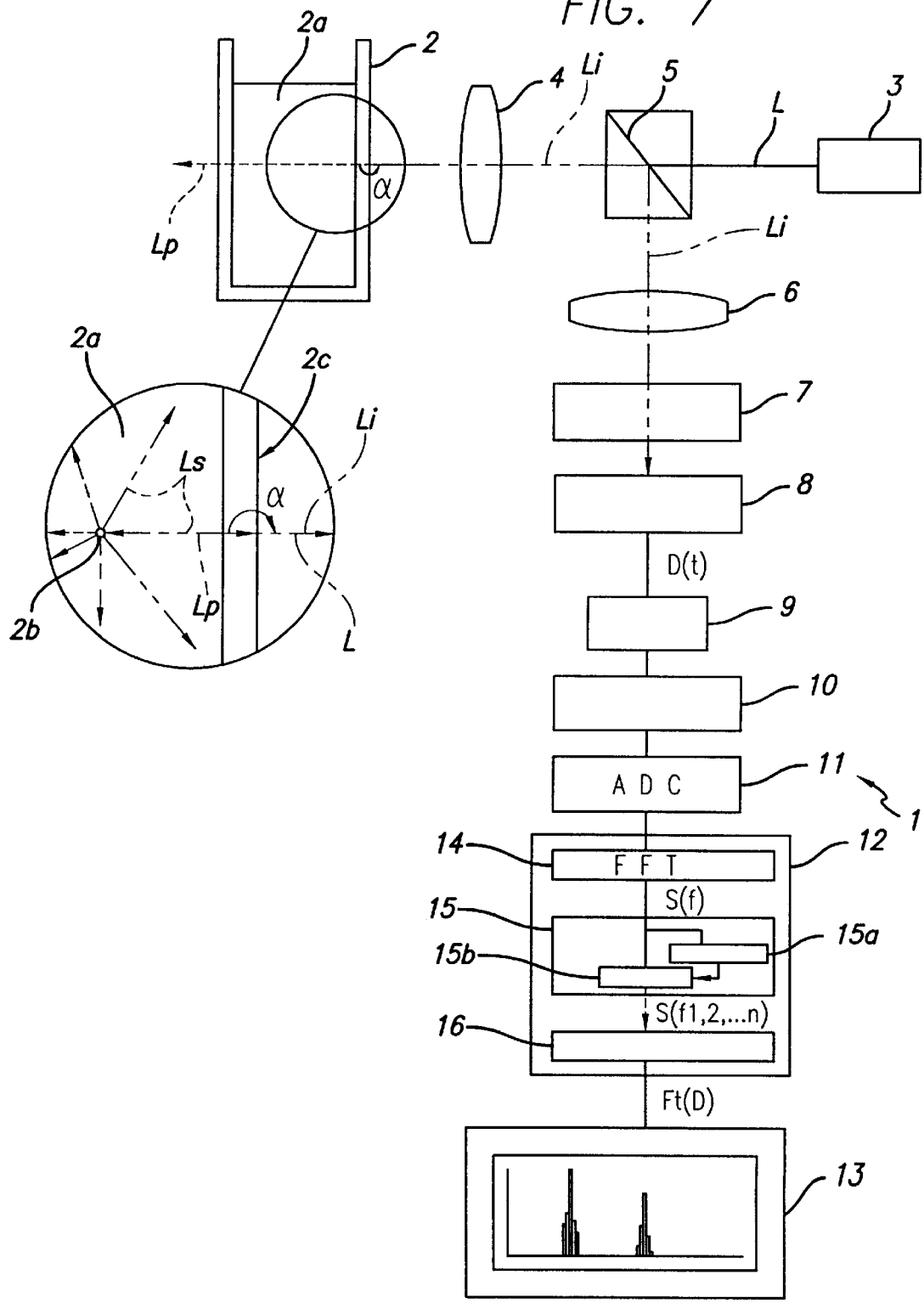
FIG. 7 is a block diagram of a particle size distribution measurement apparatus in accordance with another embodiment of the present invention.

FIG. 7 is a block diagram of an apparatus 1 for measuring the particle size distribution in accordance with another embodiment of the present invention. Since the members indicated by the same marks as those of FIG. 1 are the same or equivalent members, detailed explanation of them is omitted. In this example, the laser light L emitted from the laser light source 3 passes through the beam splitter 5 and the lens 4 and is condensed into the cell 2. At this moment, as shown in an enlarged view of FIG. 7, part of the laser light L (non-scattered light) is reflected and scattered on a wall surface 2c of the cell 2. On the other hand, the laser light Lp which has passed through the wall surface 2c scatters the laser light Ls (diffused light) which is Doppler-shifted by Brownian motion of the particles 2b dispersed in the solvent 2a. A reflection light L on the wall surface 2c and the scattered light Ls interfere with each other and turn into an interference light Li, which is condensed onto the detector 8 after passing through the lens 3, beam splitter 5, lens 6 and the polarizing plate 7.

That is, the angle α of the interference light Li with respect to the incident laser light L is 180°. The polarizing plate 7 cuts lights other than those reflected by the beam splitter 5 using polarization direction. The interference light Li is condensed into an electric detection signal D(t) by the detector 8.

Figure 8A:
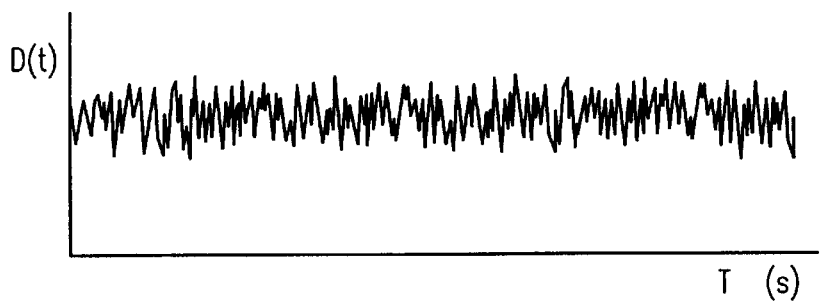
Figure 8B:
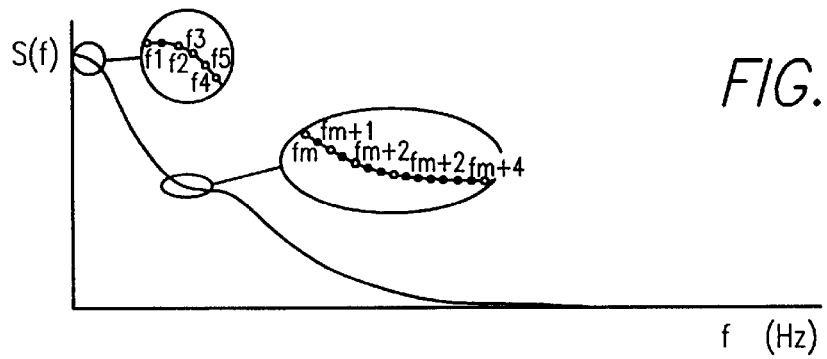

FIGS. 8A through 8D are an explanatory view for explaining the processing contents of respective parts of the measurement apparatus shown in FIG. 7, wherein particle 8b have two diameters. FIG. 8A shows detection signals D(t). FIG. 8B shows the power spectrum S(f) which has been transformed by the FFT calculation 14 and then smoothed.

Figure 8C:
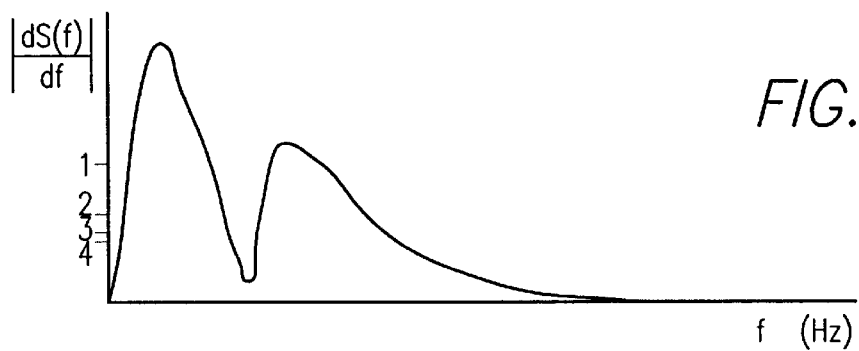

FIG. 8C shows the gradient of the power spectrum S(f) obtained by the absolute value of the first-differentiated power spectrum S(f). In accordance with the gradient, the selecting sub-unit 15b shortens the interval of data selected from the power spectrum S(f). As already described in detail, the power spectra S(f) are all extracted from the spectrum data at the extraction interval based on FIG. 8C to prepare the data table S ($f_{1, 2, 3 \ldots n}$) having the data of number n. Accordingly, as the above extraction points ($f_1$–$f_n$) are all the actually measured values, data are not interpolated as conventionally done.

Figure 8D:
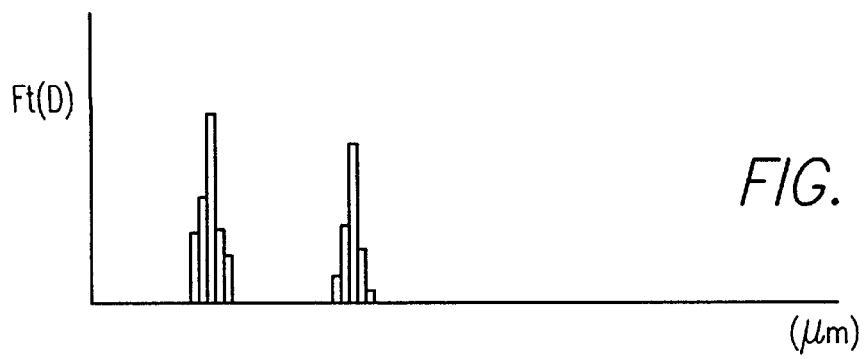

FIG. 8D shows a particle size distribution Ft(D) by performing an inverse problem based on the data table S($f_{1, 2, 3 \ldots n}$) thus selected.

As stated above, according to the particle size distribution measurement apparatus 1 of the present invention, there is no need to operate the enormous quantity of data as in the case of subjecting all the data of the power spectra S(f) to an inverse problem. Thus, a computer, which is not shown, does not require a mass storage memory for operation processing and high-speed inverse problem is made possible. Also, due to the extraction of the data table S ($f_{1, 2, 3 \ldots n}$) at the optimum extraction interval, lowering of reproducibility by deletion of data can be suppressed to the least possible extent.

In the above-stated embodiment, description has been given to a case where data is selected from the power spectrum based on the absolute values of the first-differentiated power spectrum S(f). It is noted that the present invention should not be limited to the embodiment.

FIG. 9 shows an example of selecting data from the power spectrum S(f) using the absolute values of a second-differentiated power spectrum S(f). That is, FIG. 9A shows a power spectrum S(f); FIG. 9B shows the absolute values of the first-differentiated power spectrum S(f); and FIG. 9C shows the absolute values of the second -differentiated power spectrum S(f).

Namely, in this example, the differential unit 15a obtains the absolute values of the second-differentiated power spectrum S(f), thereby obtaining the change of the gradient of the power spectrum S(f), i.e., the degree of curve of the power spectrum S(f). As indicated by the vertical axis of FIG. 9C, intervals of selecting the power spectrum S(f) are adjusted in accordance with the magnitude of the absolute value (degree of curve) of the second-differentiated power spectrum S(f). FIG. 9D shows a particle size distribution Ft(D) obtained by subjecting the selected power spectra S($f_{1, 2, 3 \ldots n}$) to an inverse problem.

According to the particle size distribution measurement apparatus 1 in this example, as in the case of the preceding embodiment, an enormous quantity of data of the power spectrum S(f) is thinned out. As a result, mass storage memory is not necessary to perform operation processing and it does not take too much time to perform an operation. In addition, data selection intervals are based on the change of gradient (degree of curve) of the power spectrum S(f). Due to this, data is selected minutely at portions where the power spectrum S(f) is sharply curved and selected roughly at portions where the power spectrum S(f) is gently curved. In other words, by performing inverse problem using the selected data table S($f_{1, 2, 3 \ldots n}$) at optimized intervals, a particle size distribution can be calculated with high accuracy even if the number of data is reduced and the deterioration of reproducibility due to the data reduction can be suppressed as much as possible.

In addition, since, as shown in each of the examples given above, the data constituting the data table S ($f_{1, 2, 3 \ldots n}$) are at all times the measured true values, measurement can be made with improved precision with preservation of high speed feature, and as there is no necessity to use extremely high speed A/D converter 11. Thus, a particle size distribution measuring apparatus 1 can be manufactured at a reduced cost.

Figure 9A:
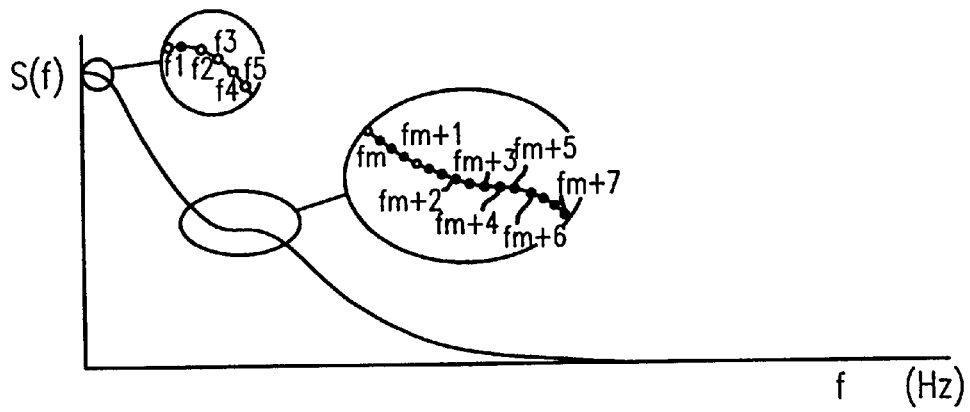
FIGS. 9A through 9D are explanatory views for explaining a modified example of the measurement apparatus, where
Figure 9B:
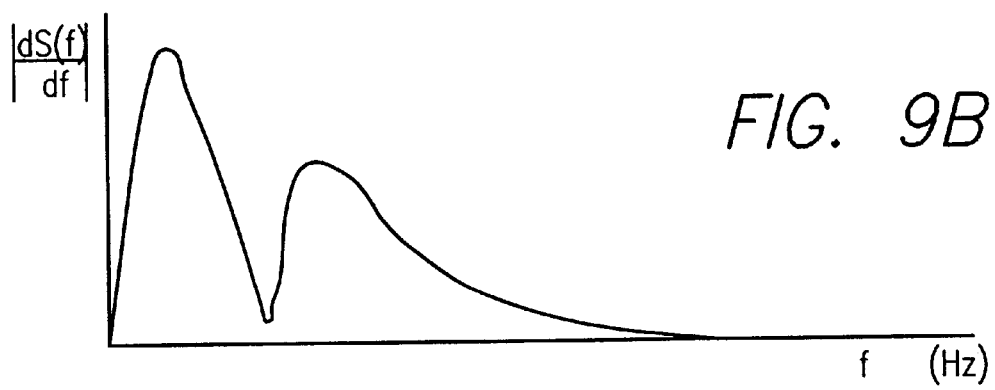
Figure 9C:
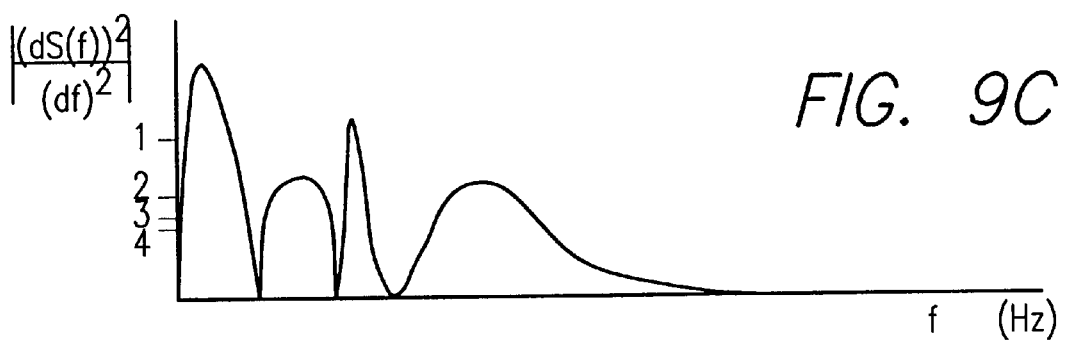
Figure 9D:
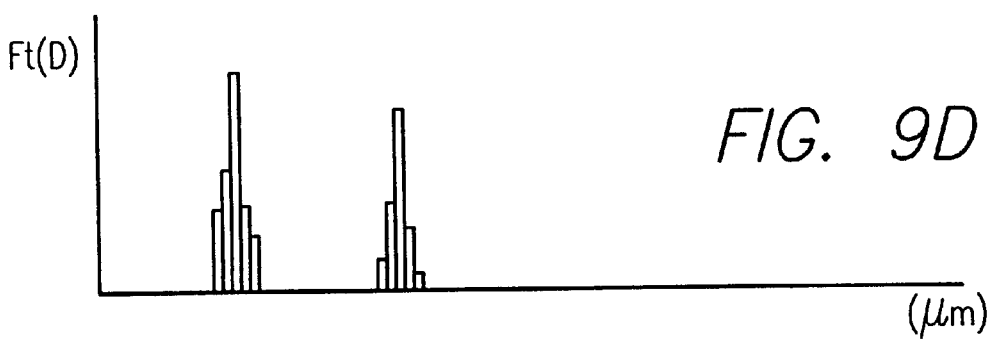

It is noted that the selection intervals shown on the vertical axes of FIGS. 8C and 9C are set with a view to preventing the deterioration of reproducibility for data selection and the reduced quantity of data. It is preferable that the setting is freely made by a user.

In the embodiments described above, basically, the power spectrum S(f) is obtained by subjecting a detection signal D(t) to Fourier transform and then smoothing. Using the power spectrum S(f) as an intermediate function, data is selected from the spectrum S(f) and subjected to inverse problem, thereby obtaining a particle size distribution. The present invention should not be limited to the use of the power spectrum S(f) as an intermediate function. For instance, the FFT 14 may subject a detection signal D(t) to a Fourier transform and then to an inverse Fourier transform to thereby obtain an autocorrelation function R(τ). The autocorrelation function R(τ) may be used as an intermediate function and subjected to an inverse problem to thereby obtain a particle size distribution Ft(D).

The relationship between autocorrelation function R(τ) and the power spectrum S(f) is shown below in expression (5), which is based on the Wiener-Khintchine formula. The autocorrelation function R(π) can be obtained by subjecting the power spectrum S(f) to an inverse Fourier transform.

$$R(\tau) = \int_{-\infty}^{\infty} S(f) e^{-if\tau} df \qquad \text{Expression (5)}$$

Thus, the FFT 14 shown in FIGS. 1 and 7 can operate the autocorrelation function R(f).

Figure 10A:
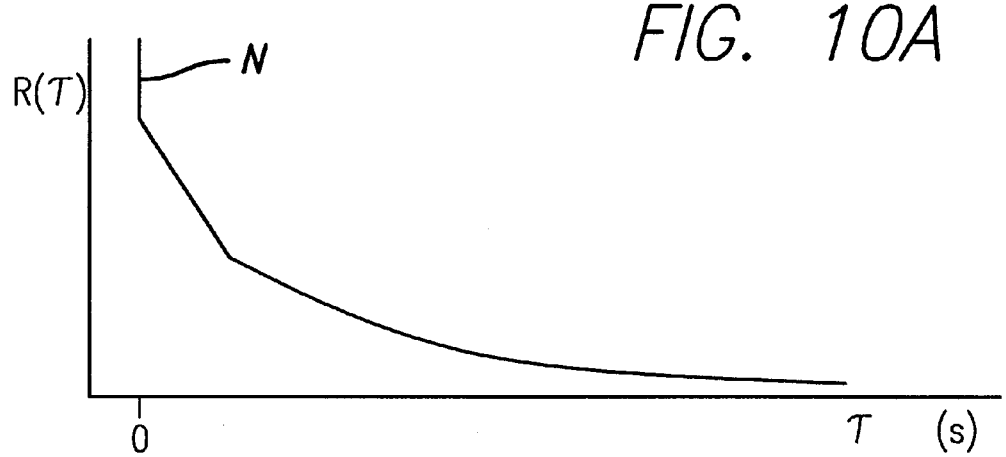
Figure 10B:
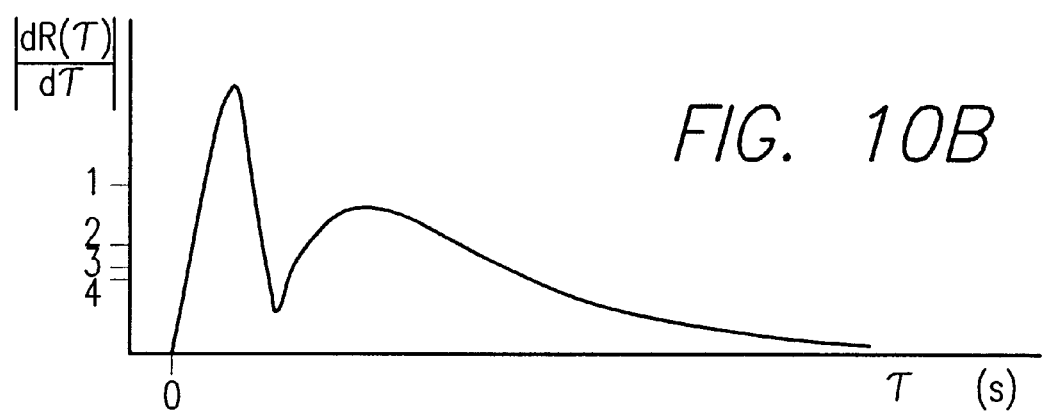
Figure 10C:
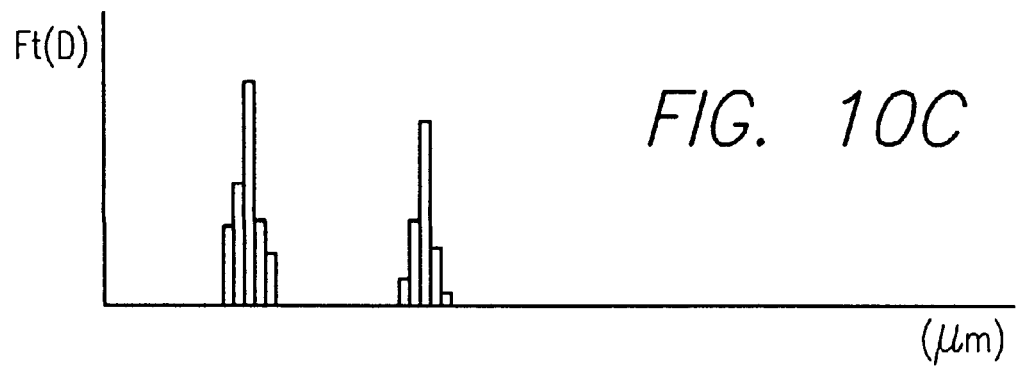

FIGS. 10A through 10C show examples of operations of the particle size distribution Ft(D) in this embodiment. As shown in FIG. 10A, if the detection signals D(t) are converted into an autocorrelation function R(r), the influence such as vibration of the solvent included in the detection signal D(t), white noise such as noise included in the output of the detector, an electric circuit, and an amplifier, or noise components N from a power supply line are concentrated into the position 0 on the horizontal axis.

By removing data on position 0 on the horizontal axis, therefore, it is possible to ensure that influences by various noise N can be removed even if smoothing processing by a software is omitted. In other words, it is possible to operate the particle size distribution Ft(D) at higher speed and measurement accuracy enhances by omitting the smoothing.

FIG. 10B shows the absolute values of the autocorrelation function R(τ) being differentiated by τ once, that is, the gradient of the autocorrelation function R(τ). In accordance with the gradient, selection intervals are narrowed and a data table R($τ_{1, 2, 3 \ldots n}$) is selected from all of the data of the autocorrelation function R(τ). FIG. 10C shows a particle size distribution obtained by operating the autocorrelation function R(τ) based on the selected data table R($τ_{1, 2, 3 \ldots n}$). A detailed description is not given in regards to the other aspects because they are the same as those shown in FIGS. 8 and 9.

In the above-stated embodiments, since the operations of the autocorrelation function R(τ) and of the power spectrum S(f) are performed by the FFT 14 (spectrum analyzer) and the like, complicated operation processing is not required and the structure of the particle size distribution measurement apparatus 1 is, thereby, made as simple as possible. However, the present invention should not be limited to them. For instance, the operation of the autocorrelation function R(τ) and the power spectrum S(f) may be performed using software. In that case, since operation speed depends on CPU performance, it is possible to shorten time required for measurement by the particle size distribution measurement apparatus 1 by using a high-speed CPU.

In each of the above-stated embodiments, an example of measuring particles of two sizes is given for the convenience of description. Needless to say, the present invention should not be limited to the case. For instance, it is possible to measure a particle size distribution at high accuracy and high speed even if monodisperse particles or polydisperse particles of three sizes of more are measured.

In either case, according to the present invention, intervals of data selection points are determined based on the gradient or change of gradient of the power spectrum S(f) or the autocorrelation function R(τ). Thus, it is possible to optimize the selection point intervals and to provide a highly accurate particle size distribution.

In the above example, as the detector 8 detects the interference light Li between the scattered light Ls by the particle 2b and the reflected light L by the wall surface 2c of the cell 2, the power spectrum in this example is a Lorentz function having a half width $DcK^2$. Also, the autocorrelation function R(τ) is an exponential function of the time constant $1/DcK^2$.

The present invention is not limited to interference light Li detection method. That is to say, although in the foregoing example the interference light Li having an angle α of 180 degrees to the laser light L is analyzed, the interference light Li may be detected in the orthogonal direction to the laser light L. In this case, the angle α is 90 degrees, and the above expression (2) is $K=2\sqrt{2}\pi n/\lambda$.

In the manner as described above, as already explained by using FIG. 4, the operation frequency characteristics $S_1$–$S_8$ of interference light Li formed from for example the particles 2b of the representative particle sizes $D_1$–$D_8$ are operated, and by using these operated frequency characteristics $S_1$–$S_8$, the particle diameter—light intensity characteristic curve $P_1$–$P_n$ representing the light intensity to the particle sizes of the respective particle diameters $D_1$–$D_8$ are obtained on the respective frequencies $f_1$–$f_n$. And, based on the particle size—light intensity characteristic curve $P_1$–$P_n$, response functions $P(f_1, D)$ –$P(f_n, D)$ are obtained.

Figure 11:
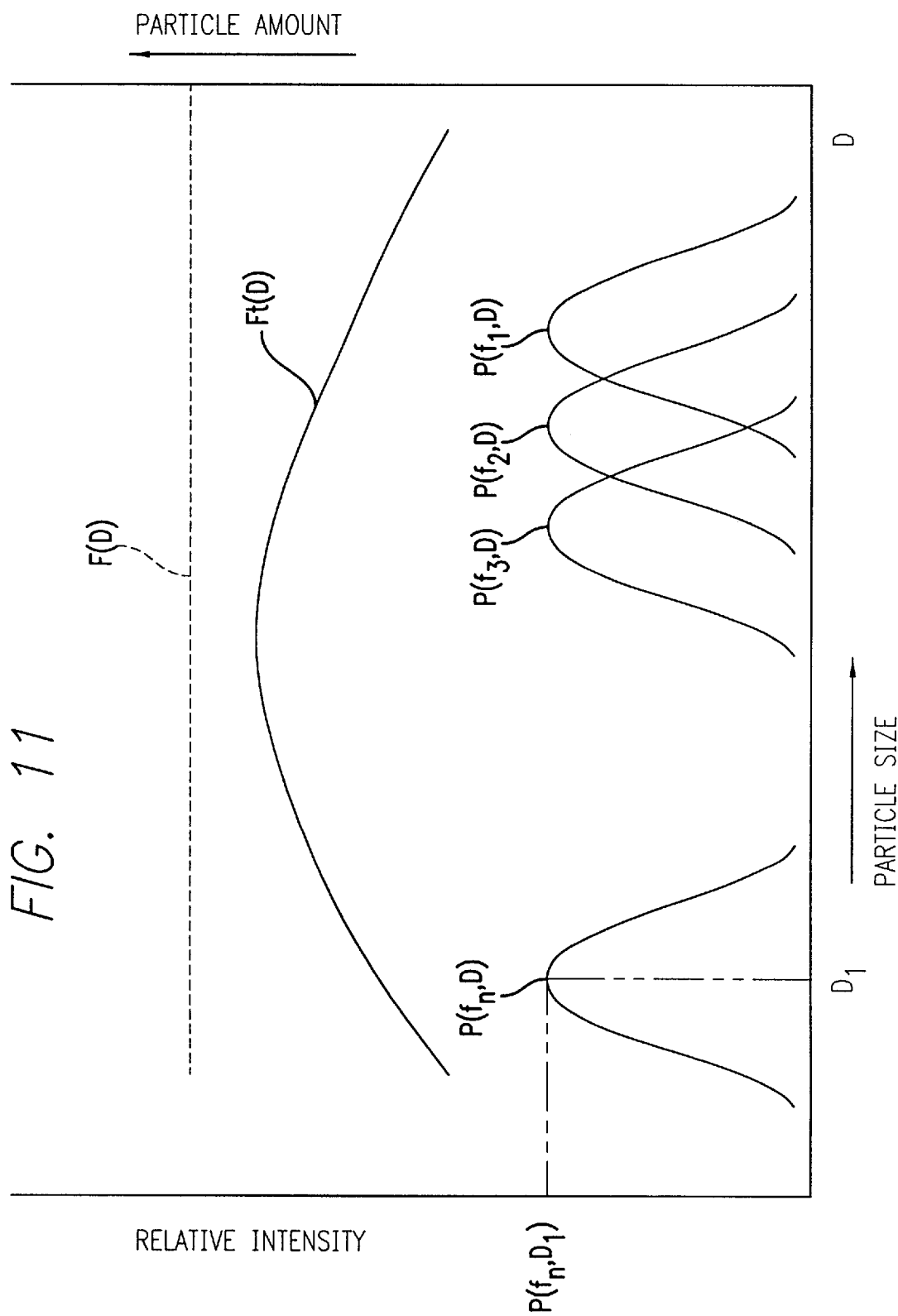
FIG. 11 shows the relationship among an assumed particle size distribution, an actual particle size distribution and a response function in the particle size distribution analysis method.
Figure 12A:
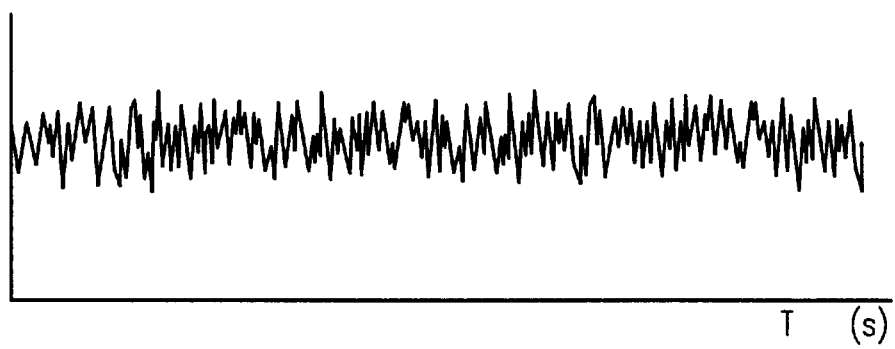
FIG. 12A shows detection signals.
Figure 12B:
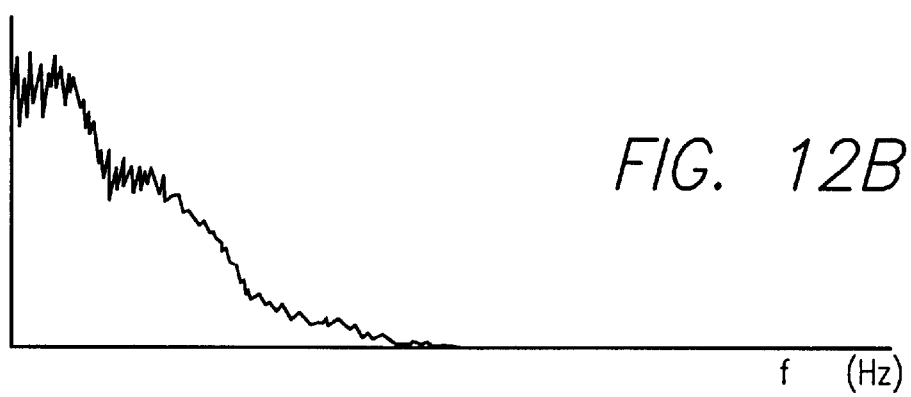
FIG. 12B shows a power spectrum.
Figure 12C:
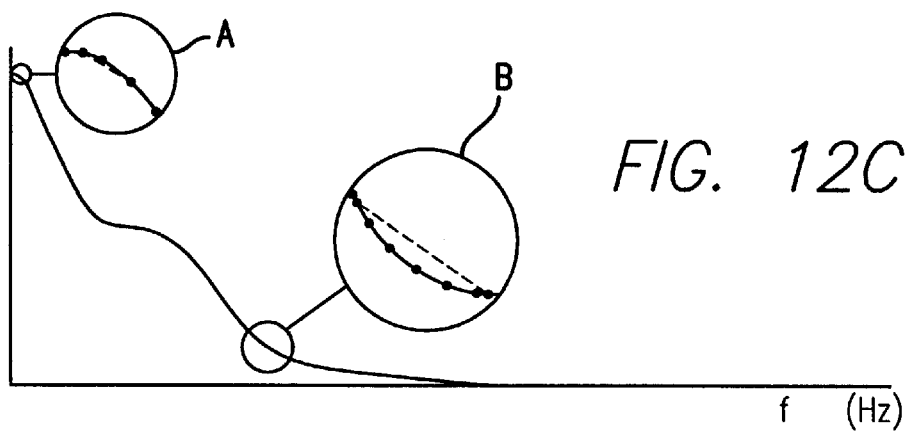
FIG. 12C shows a smoothed power spectrum.
Figure 12D:
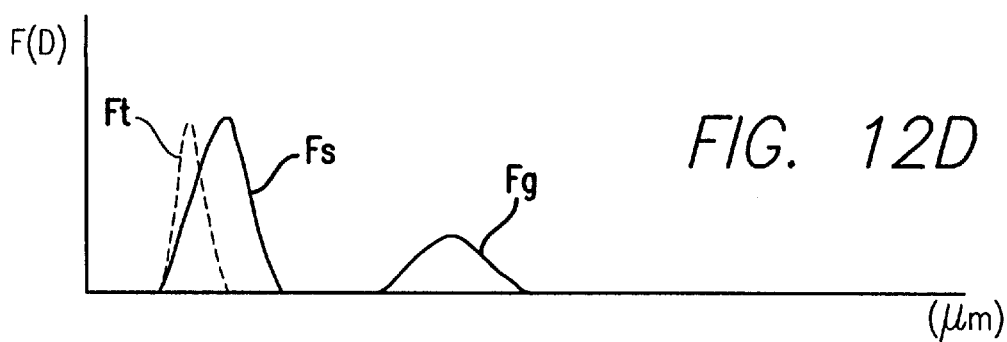
FIG. 12D shows a particle size distribution.

FIG. 11 shows response functions P(f, D) obtained as stated above. In FIG. 11, F(D) indicates an assumed particle size distribution and Ft(D) indicates a true particle size distribution. In this embodiment, the assumed particle size distribution F(D) is initially set, as shown in a virtual line in FIG. 11, for instance, such that the relative intensity is a constant value throughout the range of the particle size distribution.

FIG. 11 is a schematic diagram shown by simplification so as to facilitate to understand the present invention, and it does not show the actual values. Accordingly, the respective response functions P (f, D) are disclosed as if they were identical in the size and shape, but in practice they are not the same (functions invariable in shift).

And, as already explained with reference to FIG. 6, using the response functions $P(f_1, D) \ldots P(f_n, D)$ corresponding to the respective frequencies $f_1, f_2, \ldots f_n$ the assumed values of particle size distribution are sequentially corrected, so that, when the ratio $r_0$ of the light intensity $Sc(f_1)$ of frequency characteristic Sc(f) based on the assumed value of particle size distribution F(D) to the light intensity $S(f_1)$ of actually measured frequency characteristic S(f) approaches within a certain determined range to 1, the assumed particle size distribution F(D) is displayed on a display apparatus 13 as a true particle size distribution Ft(D).

If the response function P(f, D) is obtained, it can be operated as a curve of Lorenzian function having a half width obtained using the Stokes-Einstein expression. It is also possible to calculate fixed elements such as the angle α between the incident light L and the scattered light Li in advance.

Although description is given to a case where the response function P(f, D) is calculated based on the frequency characteristics $S_0$ to $S_7$ corresponding to particle sizes in the above embodiment, the present invention should not be limited thereto. That is, it is possible to obtain the response function P(f, D) using autocorrelation functions corresponding to particle sizes. It is possible to easily remove the noise components included in detection signals by transforming detection signals D(t) to the autocorrelation function. Thus, measurement accuracy can be enhanced as much as possible. It is noted that the present invention should not be limited to a case where the autocorrelation function is obtained by the FFT 14. The autocorrelation function may be obtained by an autocorrelation unit as a modified example.

As stated so far, according to the first and second embodiments, the data selected to create a data table used for operation is selected from all of the data regions at appropriate intervals, so that there is no need to perform interpolation operation for data lacking points and to use data shifted from true values at the time of an inverse problem.

In addition, the data selection unit may include a differential step for operating an absolute values obtained by first-differentiating the intermediate function and an extraction part for extracting data from all data regions at intervals, the intervals becoming shorter as an operation result of the differential part shows that the absolute value is higher and the intervals becoming longer as the operation result shows the absolute value is lower. Alternatively, the data extraction unit may include a differential step for operating an absolute value obtained by second-differentiating the intermediate function, and an extraction step for extracting data from all data regions at intervals, the intervals becoming shorter as an operation result of the differential part shows that the absolute value is higher and the intervals becoming longer as the operation result shows that the absolute value is lower. In either case, it is possible to thin out data having good reproducibility by selecting a small quantity of data. Thus, even with the data in small quantity, it is possible to measure a particle size distribution with high accuracy. That is, it is possible to make early measurements with high accuracy.

According to the third and fourth embodiments, the response function is calculated in accordance with measurement conditions using the Stokes-Einstein expression, so that distribution can be analyzed with high accuracy. Moreover, by comparing the frequency distribution based on the assumed particle size distribution with the measured frequency distribution and repeating the comparison while correcting the assumed particle size distribution, vibration and divergence do not occur as in the conventional method. Thus, it is possible to attain a true particle size distribution.

Additionally, as described in the fourth invention, the response function is obtained from the autocorrelation function and the measured light intensity is transformed to the autocorrelation function. As a result, it is possible to effectively remove noise components included in the detection signals and to thereby further enhance measurement accuracy.

In any of the cases described above, by using the optimum operation method, complicated operation can be avoided and operation speed can be increased. Also, it is made possible to practice an inverse problem from Category 1 Fredholm's integral equation of a non-linear subject which has so far been considered impossible to practice due to complexity, and it is possible to carry out an operation to obtain particle size distribution in as high precision as possible.

If the user appropriately selects a division width, divides the operation and display region and uses the divided sections in the operation and, for instance, if high resolution is required, it is possible to increase the number of divisions. If high resolution is not required, it is possible to decrease the number of divisions and to thereby increase speed for completing the operation. Besides, the resolution can be adjusted to that of another type of equipment so as to easily compare the obtained measurement result with that measured in another apparatus.

In particular, the present invention adopts a method of operating an operated frequency characteristic based on the assumed particle size distribution by a response function and repeating the corrections of the assumed particle size distributions while comparing it with the actually measured frequency characteristic to obtain a true particle size distribution. Due to this feature, the particle size distribution analysis according to the present invention can be performed by dividing the operation and display range in optional divisional widths and divisional numbers, so that the user can have an option to select the resolution and the operation speed.

And, by making it possible to set optionally the divisional width, divisional number, and display width as above, it becomes possible to compare the measured values with other type of apparatuses having different resolutions, which had been impossible in the past. This feature is useful in the case of making comparison with the past measurement data or the like. In the example given above, the setting is made more simple by indicating the divisional width, divisional number, and display width of operation and display range in table form, but it is possible to make the divisional width, divisional number, and display width between the representative particle sizes individually changeable.

Furthermore, in the case of not transforming the detection signal into a frequency characteristics but an autocorrelation function, it is possible to easily remove noise components included in the detection signal and to enhance the analysis accuracy of the particle size distribution.

If storing division widths, division numbers and display widths for the respective sections in a table, operating the response function and correcting the assumed particle size distribution in accordance with a division number and a division width selected from the table, and displaying the numbers of particles of the respective typical particle sizes in accordance with the selected display width, then the division width, division number and display width can be easily selected to thereby enhance operability.

What is claimed is:

1. An apparatus for measuring a particle size distribution, said apparatus comprising
   a light source directing a laser light to particles which are dispersed into a solvent and which exhibit Brownian motion;
   a detector converting an interference light caused by Doppler-shifted scattered light by the particles into an electrical detection signal;
   an operation unit obtaining an intermediate function by processing the detection signal; and
   a processing unit subjecting the intermediate function to an inverse problem and thereby calculating the particle size distribution; and
   a data selecting unit between said operation unit and said processing unit, said data selecting unit selecting data from all data regions in said intermediate function at appropriate intervals and creating a data table used in the inverse problem.

2. The apparatus according to claim 1, wherein said data selection unit includes a differential step for operating an absolute values obtained by first-differentiating the intermediate function and a selection step for selecting data from all data regions at intervals, the intervals becoming shorter as an operation result of the differential step shows that the absolute value is higher and said intervals becoming longer as the operation result shows the absolute value is lower.

3. The apparatus according to claim 1, wherein said data selection unit includes a differential step for operating an absolute value obtained by second-differentiating the intermediate function, and a selection step for selecting data from all data regions at intervals, the intervals becoming shorter as an operation result of the differential step shows that the absolute value is higher and the intervals becoming longer as the operation result shows that the absolute value is lower.

4. A method for measuring a particle size distribution, said method comprising the steps of:
   directing a laser light to particles which are dispersed into a solvent and which exhibit Brownian motion;
   converting an interference light caused by Doppler-shifted scattered light by the particles into an electric detection signal;
   processing the detected signal to obtain an interim function, followed by inversely operating the interim function to calculate a particle size distribution, wherein said method further comprising the steps of:
   selecting data from all data regions in the interim function at appropriate intervals;
   creating a data table used in the inverse problem; and
   obtaining the particle size distribution from the table.

5. The method according to claim 4, further comprising the steps of:
   operating an absolute value obtained by first-differentiating the intermediate function; and
   selecting data from all data regions at intervals, the intervals becoming shorter as an operation result of said differential step shows that the absolute value is higher and the intervals becoming longer as the operation result shows the absolute value is lower.

6. The method according to claim 4, further comprising the steps of:
   operating an absolute value obtained by second-differentiating the intermediate function; and
   selecting data from all data regions at intervals, the intervals becoming shorter as an operation result of said differential step shows that the absolute value is higher and the intervals becoming longer as the operation result shows that the absolute value is lower.

7. A method for analyzing a particle size distribution, said method comprising the steps of:
   directing a laser light to particles which are dispersed into a solvent and which exhibit Brownian motion;
   converting an interference light caused by Doppler-shifted scattered light by the particles into an electric detection signal;
   subjecting the intermediate function to an inverse problem and thereby calculating a particle size distribution, wherein said method further comprising the steps of:
   while presetting an assumed particle size distribution, calculating frequency characteristics of the detection signal and setting the frequency characteristics as measured frequency characteristics;

calculating the frequency characteristics of a Lorenzian function having a half-width obtained by a Stokes-Einstein expression from measurement conditions in accordance with particle sizes and setting the frequency characteristics of the Lorenzian function as operation frequency characteristics;

calculating a response function indicating a light intensity with respect to a particle size based on the operation frequency characteristics for every frequency;

calculating the frequency characteristics based on assumed values in the assumed particle size distribution for every frequency using the response function as a weight;

correcting the assumed particle size distribution in accordance with a rate of a difference between the frequency characteristics based on the assumed values and the measured frequency characteristics;

repeating said processing steps using the corrected assumed particle size distribution;

determining, as a true particle size distribution, the assumed particle size distribution when the rate of the difference between the frequency characteristics based on the assumed values and the measured frequency characteristics falls within a predetermined range.

8. The method according to claim 7, further comprising the steps of:

dividing an operation and display range of the particle size distribution into sections, each section having an appropriate division width selected by a user;

determining typical particle sizes for the respective sections; and displaying the number of particles of respective typical particle sizes on a true particle size distribution obtained while using the number of particles of the respective typical particle sizes as an assumed particle size distribution.

9. The method according to claim 8, further comprising the steps of:

storing division widths, division numbers and display widths for the respective sections in a table;

operating the response function and correcting the assumed particle size distribution in accordance with a division number and a division width selected from said table; and displaying the numbers of particles of the respective typical particle sizes in accordance with the selected display width.

10. A method for analyzing a particle size distribution, said method comprising the steps of:

directing a laser light to particles which are dispersed into a solvent and which exhibit Brownian motion;

converting an interference light caused by Doppler-shifted scattered light by the particles into an electric detection signal;

subjecting the intermediate function to an inverse problem and thereby calculating a particle size distribution, wherein said method further comprising the steps of:

while presetting an assumed particle size distribution, calculating an autocorrelation function of the detection signal and setting the autocorrelation function as a measured autocorrelation function;

calculating an autocorrelation function of an exponential function having a time constant obtained by a Stokes-Einstein expression from measurement conditions in accordance with a particle size and setting the autocorrelation function as an operation autocorrelation function;

calculating a response function indicating a light intensity with respect to a particle size based on the operation autocorrelation function for every delay time;

calculating the autocorrelation function based on assumed values in the assumed particle size distribution for every delay time using the response function as a weight;

correcting the assumed particle size distribution in accordance with a rate of a difference between the autocorrelation function based on the assumed values and the measured autocorrelation function;

repeating said processing steps using the corrected assumed particle size distribution;

determining, as a true particle size distribution, the assumed particle size distribution when the rate of the difference between the autocorrelation function based on the assumed values and the measured autocorrelation function falls within a predetermined range.

11. The method according to claim 10, further comprising the steps of:

dividing an operation and display range of the particle size distribution into sections, each section having an appropriate division width selected by a user;

determining typical particle sizes for the respective sections; and displaying the number of particles of respective typical particle sizes on a true particle size distribution obtained while using the number of particles of the respective typical particle sizes as an assumed particle size distribution.

12. The method according to claim 11, further comprising the steps of:

storing division widths, division numbers and display widths for the respective sections in a table;

operating the response function and correcting the assumed particle size distribution in accordance with a division number and a division width selected from said table; and displaying the numbers of particles of the respective typical particle sizes in accordance with the selected display width.

* * * * *